US006841368B1

(12) United States Patent
Rhee et al.

(10) Patent No.: US 6,841,368 B1
(45) Date of Patent: Jan. 11, 2005

(54) ENZYMATIC PRODUCTION OF DIFRUCTOSE DIANHYDRIDE IV FROM SUCROSE AND RELEVANT ENZYMES AND GENES CODING FOR THEM

(75) Inventors: Sangki Rhee, Seoul (KR); Kibang Song, Taejon (KR); Chulho Kim, Taejon (KR); Eunja Ryu, Taejon (KR); Yongbok Lee, Gwangiu (KR)

(73) Assignees: Korea Research Institute of Bioscience and Biotechnology, Taejon (KR); Realbiotech Ltd., Taejon (KR)

( * ) Notice: Subject to any disclaimer, the term of this patent is extended or adjusted under 35 U.S.C. 154(b) by 11 days.

(21) Appl. No.: 09/868,328

(22) PCT Filed: Oct. 19, 2000

(86) PCT No.: PCT/KR00/01183

§ 371 (c)(1),
(2), (4) Date: Nov. 9, 2001

(87) PCT Pub. No.: WO01/29185

PCT Pub. Date: Apr. 26, 2001

(30) Foreign Application Priority Data

Oct. 19, 1999 (KR) ........................................ 1999/45302

(51) Int. Cl.$^7$ ............................ C12N 9/00; C12N 9/12; C12N 1/20; C12N 15/00; C07H 21/04

(52) U.S. Cl. .............................. 435/194; 435/4; 435/6; 435/69.1; 435/183; 435/193 T; 435/252.3; 435/320.1; 536/23.2

(58) Field of Search .............................. 435/4, 6, 69.1, 435/183, 193 T, 194, 252.3, 320.1, 69.2, 193; 536/23.2 T, 23.2, 23.7; 530/412, 413

(56) References Cited

PUBLICATIONS

NIOC (GenBank Accession No. AAY04105 Jun. 10, 1999).*

Tanaka (a)et al. (J. Biochem., 1983, vol. 94(5):1569–1578).*

Tanaka (a)et al. (J. Biochem., 1985, vol. 97(6):1679–88).*

Song et al. (SPTREMBL Accession No. Q9KJD0, Oct. 1, 2000).*

Lee et al., *Federation of Microbiological Societies (FEMS) Microbiology Letters,* vol. 195, pp. 127–132, 2001.

Song et al., *Enzyme and Microbial Technology,* vol. 27, pp. 212–218, 2000.

* cited by examiner

*Primary Examiner*—Manjunath N. Rao
(74) *Attorney, Agent, or Firm*—Nath & Associates PLLC; Gary M. Nath; Lee C. Heiman

(57) ABSTRACT

Disclosed is the production of difructose dianhydride IV from sugar. A sugar solution is subjected to reaction at room temperature or lower in an acidic buffer of pH 3.0–7.0 in the presence of a levansucrase derived from *Z. mobilis* to produce levan. The levansucrase is prepared by culturing *E. coli* BL21 (DE3)/pEL12 (KCTC 8661), harvesting and homogenizing the cells, and isolating levansucrase from the cell homogenate. Levan is purified from the reaction solution and subjected to reaction at 25–50° C. for 3–10 hours in an acidic buffer of pH 3.0–7.0 in the presence of a levan fructotransferase to produce difructose dianhydride IV. The levan fructotransferase is obtained from *E. coli* JUD81 (KCTC 0877BP). Also, disclosed are a gene coding for the levan fructotransferase and an expression vector pUDAF81 carrying the gene.

3 Claims, 9 Drawing Sheets

Figure 3

SEQ ID NO: 5 (DNA sequence)
SEQ ID NO: 6 (Protein sequence)

```
aaatataaat ataaatttag ttttaagtaa aaacttccga aaaaaatgtg acttcgcttg     60
aaatgtcgaa gcgtgtcttt cgaaaaggca gcctatttca atatttctgc ccttttgaaa    120
gtcgagaaca agaattaatc tttttcggc tttatttcat catttattag gatagttctt     180
atg ttg aat aaa gca ggc att gca gag ccg agc ttg tgg act cgt gcg      228
Met Leu Asn Lys Ala Gly Ile Ala Glu Pro Ser Leu Trp Thr Arg Ala
1               5                   10                  15
gat gct atg aaa gtg cat acc gat gat ccc acg gca acc atg cct acc      276
Asp Ala Met Lys Val His Thr Asp Asp Pro Thr Ala Thr Met Pro Thr
            20                  25                  30
att gat tat gac ttt cct gtc atg act gat aaa tat tgg gtt tgg gac      324
Ile Asp Tyr Asp Phe Pro Val Met Thr Asp Lys Tyr Trp Val Trp Asp
        35                  40                  45
act tgg ccc tta cgc gat att aac ggt cag gtt gtc agc ttc caa ggt      372
Thr Trp Pro Leu Arg Asp Ile Asn Gly Gln Val Val Ser Phe Gln Gly
    50                  55                  60
tgg tcg gtg atc ttt gct ttg gtc gct gat cgc acc aaa tat ggt tgg      420
Trp Ser Val Ile Phe Ala Leu Val Ala Asp Arg Thr Lys Tyr Gly Trp
65                  70                  75                  80
cat aat cgc aat gat ggc gcc aga att ggt tat ttc tat tca cgt ggt      468
His Asn Arg Asn Asp Gly Ala Arg Ile Gly Tyr Phe Tyr Ser Arg Gly
                85                  90                  95
gga agc aac tgg att ttt ggt ggt cat ctt ctg aaa gat ggt gcc aat      516
Gly Ser Asn Trp Ile Phe Gly Gly His Leu Leu Lys Asp Gly Ala Asn
            100                 105                 110
ccg cgt tct tgg gaa tgg tct ggt tgc acg att atg gca ccg ggt acg      564
Pro Arg Ser Trp Glu Trp Ser Gly Cys Thr Ile Met Ala Pro Gly Thr
        115                 120                 125
gcc aat tct gtc gaa gta ttc ttt acg tct gtc aat gat acg ccg tca      612
Ala Asn Ser Val Glu Val Phe Phe Thr Ser Val Asn Asp Thr Pro Ser
    130                 135                 140
gaa tcc gtt cct gcc cag tgc aag ggc tac atc tat gcc gat gat aaa      660
Glu Ser Val Pro Ala Gln Cys Lys Gly Tyr Ile Tyr Ala Asp Asp Lys
145                 150                 155                 160
tcg gta tgg ttt gac ggt ttt gat aaa gtg acc gat ctg ttt cag gca      708
Ser Val Trp Phe Asp Gly Phe Asp Lys Val Thr Asp Leu Phe Gln Ala
                165                 170                 175
gat ggc ctt tat tat gct gat tat gca gaa aat aat ttc tgg gat ttc      756
Asp Gly Leu Tyr Tyr Ala Asp Tyr Ala Glu Asn Asn Phe Trp Asp Phe
            180                 185                 190
cgc gat ccg cat gtc ttc att acc ccg aag ata ggc aaa aca tat gcc      804
Arg Asp Pro His Val Phe Ile Thr Pro Lys Ile Gly Lys Thr Tyr Ala
        195                 200                 205
ttg ttt gaa ggt aat gtt gcc atg gag cgc ggt acg gtc gct gtt ggc      852
Leu Phe Glu Gly Asn Val Ala Met Glu Arg Gly Thr Val Ala Val Gly
    210                 215                 220
gaa gag gaa att ggc cct gtt cca cca aaa acc gaa acg cct gat ggc      900
Glu Glu Glu Ile Gly Pro Val Pro Pro Lys Thr Glu Thr Pro Asp Gly
225                 230                 235                 240
gct cgc tat tgt gct gct gcc att ggt att gca cag gcc ctt aat gaa      948
Ala Arg Tyr Cys Ala Ala Ala Ile Gly Ile Ala Gln Ala Leu Asn Glu
                245                 250                 255
gcc cgc acc gaa tgg aaa ttg tta ccg cct ttg gta acc gcc ttt ggt      996
Ala Arg Thr Glu Trp Lys Leu Leu Pro Pro Leu Val Thr Ala Phe Gly
            260                 265                 270
gtc aat gac cag acg gag cgg cct cat gtc gtt ttc cag aat ggc ttg     1044
Val Asn Asp Gln Thr Glu Arg Pro His Val Val Phe Gln Asn Gly Leu
        275                 280                 285
acc tat ctc ttt acg atc agt cat cat tcg act tat gcc gat ggt ttg     1092
Thr Tyr Leu Phe Thr Ile Ser His His Ser Thr Tyr Ala Asp Gly Leu
    290                 295                 300
tcg ggt cct gat ggg gtt tat ggc ttt gtt tct gaa aac ggc att ttt     1140
Ser Gly Pro Asp Gly Val Tyr Gly Phe Val Ser Glu Asn Gly Ile Phe
305                 310                 315                 320
ggc cct tat gaa ccg ctg aat ggt tcc ggt ttg gtt ctc ggt aac ccc     1188
Gly Pro Tyr Glu Pro Leu Asn Gly Ser Gly Leu Val Leu Gly Asn Pro
                325                 330                 335
tct tca cag cct tat cag gct tat tcc cat tat gtg atg aca aat ggg     1236
Ser Ser Gln Pro Tyr Gln Ala Tyr Ser His Tyr Val Met Thr Asn Gly
            340                 345                 350
ctg gtg acc tcc ttc att gat acc att ccg agt tct gac ccg aat gtc     1284
Leu Val Thr Ser Phe Ile Asp Thr Ile Pro Ser Ser Asp Pro Asn Val
        355                 360                 365
tat cgt tat ggt ggc acc ttg gca ccg acc atc aaa ttg gaa ttg gtt     1332
Tyr Arg Tyr Gly Gly Thr Leu Ala Pro Thr Ile Lys Leu Glu Leu Val
    370                 375                 380
ggc cat cgc agc ttc gtt acc gaa gtg aag ggt tat ggc tat att ccg     1380
Gly His Arg Ser Phe Val Thr Glu Val Lys Gly Tyr Gly Tyr Ile Pro
385                 390                 395                 400
cca cag atc gag tgg ttg gca gaa gat gaa tct tct aat tct gcg gca     1428
Pro Gln Ile Glu Trp Leu Ala Glu Asp Glu Ser Ser Asn Ser Ala Ala
                405                 410                 415
gcc ctg tct tta ttg aat aaa taagatttat tcattgtaaa tgacgtttct        1479
Ala Leu Ser Leu Leu Asn Lys
            420
gattatgctt gaatcaagca ttatcatctt ttgagtttat ttcaacttaa gggtcatcag   1539
ggcatttcgc cctgatgaca cccttcctat tcctaataat aatttcaaga aagtgtatac   1599
tactttaaat gtttaatttt aatgccagtc gctggacgcg agcccaagcg atgaaagtga   1659
ataaatttga tttgacgacc tctatgccgg aaatcggcac tgatttcccc attatgcgtg   1719
atgacttgtg gctgtgggat acttggccat tacgggatat caatggcaat cctgtcagct   1779
ttaaaggctg gaatgttatt t
```

ENZYMATIC PRODUCTION OF DIFRUCTOSE DIANHYDRIDE IV FROM SUCROSE AND RELEVANT ENZYMES AND GENES CODING FOR THEM

TECHNICAL FIELD

The present invention relates to the enzymatic production of difructose dianhydride IV (hereinafter referred to as "DFA IV") from sucrose. More particularly, the present invention relates to enzymes which take part in the production of DFA IV from sugar and their use. In addition, the present invention relates to the production of the intermediate product during the production of DFA IV. Also, the present invention is concerned with novel genes coding for the enzymes, expression vectors carrying the genes, and transformed cells with the expression vectors.

BACKGROUND ART

Difructose dianhydride was first found in 1929 by Jackson et al. by analyzing a by-product which was produced when inulin was treated with sulfuric acid to prepare a fructose syrup. Difructose dianhydride, a kind of a cyclic disaccharide, consists of two fructose residues in which a reducing end of each residue is linked to a non-reducing hydroxy group of the counter residue. There have been discovered five kinds of difructose dianhydride, named DFA I to DFA V, thus far. Of them, DFA II and V are found to be synthesized only chemically while the others can be produced enzymatically: DFA I and III are produced from inulin by the action of inulin fructotransferase; and DFA IV from levan by the action of levan fructotransferase.

Difructose dianhydride is a non-digestive, non-fermentative sub-saccharide which is not digested in the animal body. In addition to being useful as a low-calorie sweetener, the sub-saccharide plays a role in inhibiting tooth decay and as a productive factor for *Bifidus* bacteria. It is also reported that difructose dianhydride is used as an absorption factor of minerals in the body (Baik, B. H, Lee, Y. W., and Lee, Y. B.; U.S. Pat. No. 5,700,832, UK. Pat. No. GB 2 308 547 A, Japanese Pat. Appl'n No. 8-51370, Korean Pat. Laid-Open Publication No. 96-13376, Sakurai et al., 1997).

Representative of polyfructans, inulin and levan, both naturally occurring fructose homopolysaccharides, are used to prepare difructose dianhydride (Han, 1989). From them, difructose dianhydride can be synthesized chemically or enzymatically. Chemical synthesis of difructose dianhydride from the natural polyfructans, however, suffers from significant disadvantages. For example, chemical synthesis is of low reaction selectivity, followed by complicated separation and purification. What is worse, it produces pollution of the environment. Consequently, these problems do not vest economical production value in the chemical synthesis. In contrast, enzymatic synthesis using bio-catalysts, such as microbes or enzymes, is now regarded as being very economically favorable in synthesizing difructose dianhydride from the natural polyfructans.

Since the discovery of difructose dianhydride III synthase (inulin fructotransferase) from microbes by Tanaka in 1972, enzymes that have the function of synthesizing difructose dianhydrides have been isolated from several microbial sources. The difructose dianhydrides which can be synthesized by such microbe-derived enzymes include DFA I, III and IV. DFA IV is synthesized from levan by the catalytic action of levan fructotransferase and two microorganisms, *Arthrobacter ureafaciens* and *Arthrobacter nicotinovorans* GS-9 are found to produce DFA IV.

Only a very small amount of levan fructotransferase is synthesized from these bacteria and, thus, its use in the production of difructose dianhydride is very unfavorable in terms of technical and economical aspects. Now generally, in order to obtain a large amount of a gene of interest, a gene recombinant technique is employed. That is, a levan fructotransferase gene is first isolated from its microbial source and cloned, followed by mass-expression in *E. coli.* Of the levan fructotransferase-producing strains discovered so far, only *A. nicotinovorans* GS-9 is achieved in cloning its levan fructotransferase gene.

Being a substrate of levan fructotransferase to produce DFA IV, levan, a homopolysaccharide of fructose, is prepared from sucrose by the transfructosylation reaction of levansucrase. The enzymes which can catalyze the hydrolysis of sucrose are exemplified by sucrase (beta-D-fructofuranosidase, EC 3.2.1.26), levanase (beta-2,6-D-fructan fructanohydrolase, EC 3.2.1.65), levansucrase (beta-2,6-fructan: D-glucose-1-fructosyl transferase, EC 2.4.1.10), maltase (alpha-D-glucoside glucohydrolase, EC 3.2.1.20), etc. Levan can be produced from sucrose by taking advantage of the transfructosylation activity of levansucrase (Tanaka & Yamamoto, *J. Biochem.,* 85, 287 (1979)).

There are disclosed methods for the production of levan using levansucrase. For example, it is described in U.S. Pat. No. 4,879,228 and International Publication No. WO 86-4091 that levan is produced by a fermentation process in which advantage is taken of the microbes employing sucrose in their metabolism. The patents, however, suffer from many problems. There is required a lengthy culture period to produce levan. Further, because the culture contains various products, a difficult purification procedure is needed, giving rise to a decrease in the production yield of levan. When account is taken of these problems, an enzyme reaction process has an advantage over the culture process in that, because the products of levansucrase are dependent on the reaction conditions for the production of levan from sucrose, desirable products can be obtained by controlling the conditions with ease.

It is reported that levan finds numerous applications in the medicinal field, such as a serum substituent (Dedonder et al., *Bull. Soc. Chim. Biol.,* 39, 438 (1957); Schechter et al., *J. Lab. Clin. Med.,* 61, 962(1963)), a colloid stabilizer, an immune agent, a pharmacological enhancer, etc. (Leibovici et al., *Anticancer Res.,* 5, 553 (1985); Stark et al., *Br. J. Exp. Path.,* 67, 141 (1986)), the foodstuffs field, such as quality improver, a stabilizer, an additive for health food, etc. (Hatcher et al., *Bioprocess, Technol.,* 11, 1(1989)), the typographic field, and the cosmetic field (Whiting et al., *J. Inst. Brew.,* 73, 422 (1967); Han, *Bioprocess Technol.,* 12, 1(1920)).

DISCLOSURE OF THE INVENTION

It is an object of the present invention to provide an enzymatic process for producing levan from sugar at a high yield.

It is another object of the present invention to provide a levansucrase gene derived from *Z. mobilis,* which contains such a specific tool as to allow its protein to be purified with ease.

It is a further object of the present invention to provide a recombinant expression vector carrying a levansucrase gene derived from *Z. mobilis,* which can express levansucrase in *E. coli.*

It is still a further object of the present invention to provide a bacterial species which is transformed by the recombinant expression vector and can produce levansucrase.

It is yet a further object of the present invention to provide a process of preparing levansucrase by taking advantage of the transformed bacteria.

It is still another object of the present invention to provide an enzymatic process for producing DFA IV from levan at a high yield.

It is yet another object of the present invention to provide a novel bacteria *A. ureafaciens* K2032, which produces levan fructotransferase.

It is yet another object of the present invention to provide a novel gene coding for levan fructotransferase, derived from *A. ureafaciens* K2032.

It is yet another object of the present invention to provide a recombinant levan fructotransferase gene, which contains such a specific tool as to allow its protein to be purified with ease.

It is yet another object of the present invention to provide a recombinant expression vector carrying the recombinant gene and a bacterial species which anchors the recombinant expression vector.

It is yet another object of the present invention to provide a process of preparing levan fructotransferase by taking advantage of the transformed bacteria.

It is yet another object of the present invention to provide an enzymatic process for producing DFA IV from sucrose at a high yield by utilizing the levansucrase and the levan fructotransferase.

In accordance with a first embodiment of the present invention, there is provided a process for producing levan from sugar, in which a sugar solution is subjected to reaction at room temperature or lower in an acidic buffer of pH 3.0–7.0 in the presence of a levansucrase derived from *Z. mobilis.* In one version of this embodiment, the reaction is carried out at 0–15° C. and the sugar solution has a sugar concentration of 10–30% (w/v).

In accordance with a fourth embodiment of the present invention, there is provided a recombinant expression vector, carrying the levansucrase gene.

In accordance with a fifth embodiment of the present invention, there is provided a novel bacteria *E. coli* BL21 (DE3)/pEL12 (KCTC 8661), in which the plasmid carries a levansucrase gene derived from *Z. mobilis.*

In accordance with a sixth embodiment of the present invention, there is provided a process of preparing levansucrase, comprising the steps of culturing a bacterial species anchoring a levansucrase gene-carrying, expression plasmid, harvesting and homogenizing the cells, and isolating levansucrase from the cell homogenate. In one version of this embodiment, the levansucrase gene has a base sequence stretch encoding histidine residues at its 5'- or 3'-end. In another version of this embodiment, the isolating step is carried out using metal ion-affinity chromatography and the bacterial species is *E. coli* BL21(DE3)/pEL12 (KCTC 8661P).

In accordance with a seventh embodiment of the present invention, there is provided a novel microorganism *A. ureafaciens* K2032, which shows an activity of selectively producing difructose dianhydride IV from levan and an activity of degrading levan.

In accordance with an eighth embodiment of the present invention, there is provided a novel levan fructotransferase of SEQ ID. NO: 1.

In accordance with a ninth embodiment of the present invention, there is provided a novel levan fructotransferase polynucleotide of SEQ ID NO: 2.

In accordance with a tenth embodiment of the present invention, there is provided a novel levan fructotransferase of SEQ ID NO: 1 encoded by a polynucleotide of SEQ ID NO: 2, as provided in the composite polynucleotide/amino acid sequence of SEQ ID NO: 3.

In accordance with an eleventh embodiment of the present invention, there is provided a recombinant expression vector, carrying the levan fructotransferase gene.

In accordance with a twelfth embodiment of the present invention, there is provided a process for producing DFA IV from levan, in which a levan solution is subjected to reaction at 25–50° C. for 3–10 hours in an acidic buffer of pH 3.0–7.0 in the presence of a levan fructotransferase. In one version of this embodiment, the reaction is carried out at 37° C. In another version of this embodiment, the acidic buffer is a phosphate buffer of pH 5.8 and the levan solution has a levan concentration of 5–15% (w/v).

In accordance with a thirteenth embodiment of the present invention, there is provided a process of preparing levan fructotransferase, comprising the steps of culturing a bacterial species anchoring a levan fructotransferase gene-carrying, expression plasmid, harvesting and homogenizing the cells, and isolating levan fructotransferase from the cell homogenate. In one version of this embodiment, the levan fructotransferase has histidine residues at its N- or C-terminus and the isolating step is carried out using metal ion-affinity chromatography.

In accordance with an fourteenth embodiment of the present invention, there is provided a process for producing difructose dianhydride IV from sucrose, comprising the steps of reacting a sugar solution at room temperature or lower in an acidic buffer of pH 3.0–7.0 in the presence of a levansucrase to produce levan, purifying the levan from the sugar reaction mixture, partially or completely, reacting a levan solution at 25–50° C. for 3–10 hours in an acidic buffer of pH 3.0–7.0 in the presence of a levan fructotransferase to produce difructose dianhydride IV, and isolating the difructose dianhydride IV from the levan reaction mixture.

BRIEF DESCRIPTION OF THE DRAWINGS

The above and other objects, features and other advantages of the present invention will be more clearly understood from the following detailed description taken in conjunction with the accompanying drawings, in which:

FIG. 3 shows a base sequence of the levansucrase gene (SEQ ID NO. 5) and an amino acid sequence deduced therefrom (SEQ ID NO. 6).

BEST MODE FOR CARRYING OUT THE INVENTION

Figure 1:
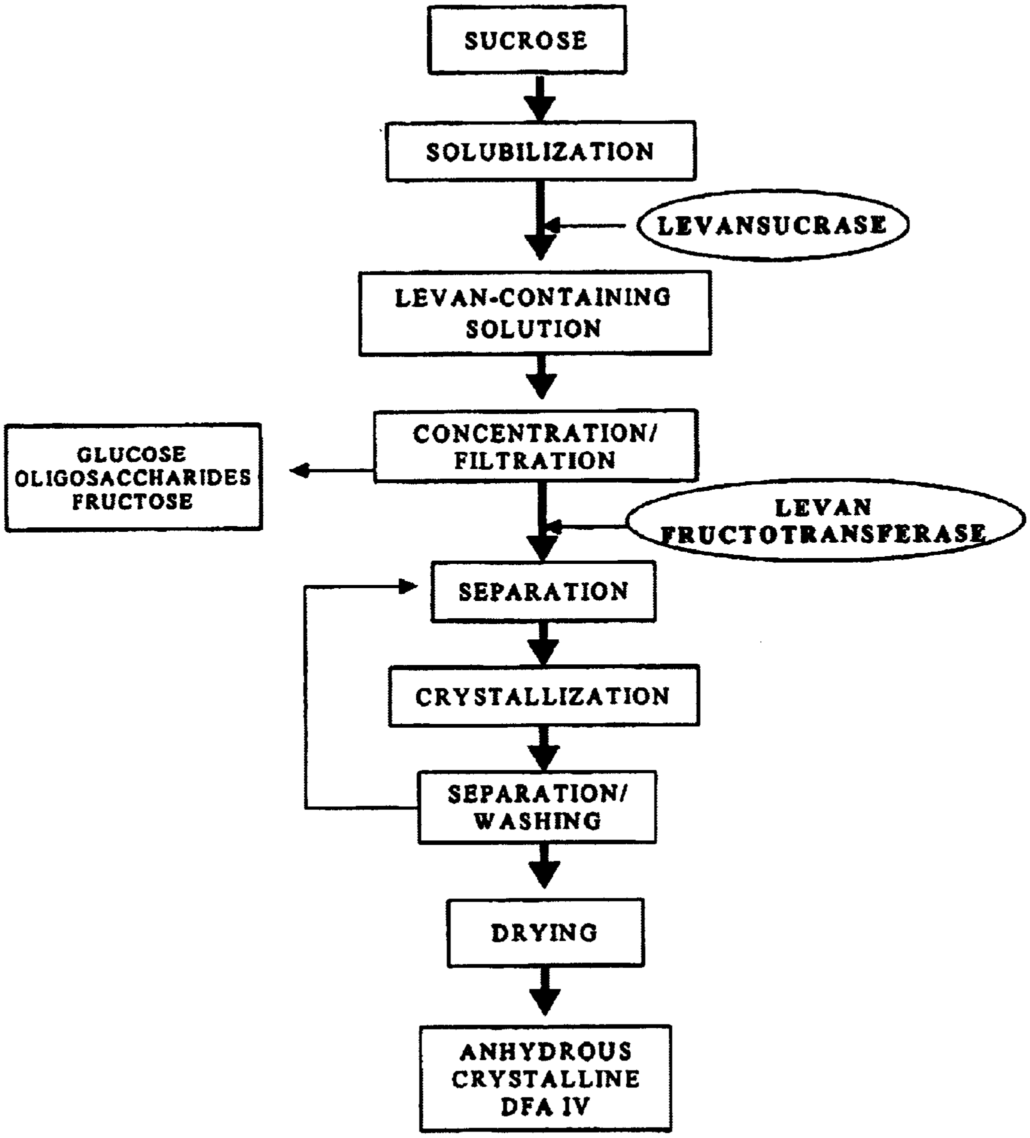
FIG. 1 shows the various steps in a process for the production of difructose dianhydride IV from sucrose.

The present invention pertains to the enzymatic production of DFA IV from sucrose, which is achieved by carrying out the following process steps: a levan production process by levansucrase, a purification and concentration process of levan, a DFA IV production process by levan fructotransferase, and a DFA IV recovery process by crystallization. Below, a description will be given, in detail, of these processes (FIG. 1).

1. Levan Production Process by Levansucrase

In accordance with the present invention, the production of levan is based on the catalysis of the levansucrase isolated from *Z. mobilis* with sucrose serving as a substrate. In the presence of the levansucrase, sucrose is subjected to reaction at room temperature, preferably at 0–15° C. and more preferably at 10° C. for 20–80 hours and preferably for 20 hours in an acidic buffer solution of pH 3.0–7.0 and preferably of pH 5.0. Therefore, most preferable is to react the sucrose at 10° C. for 20 hours in an acetic acid buffer of pH 5.0.

As for the substrate, its examples include refined sugar and raw sugar with preference to refined sugar.

The sugar preferably has a concentration of 10–30% (w/v) based on the total volume of the culture and most preferably 20% (w/v).

Regardless of whether it is natural or is made by genetic recombination, the levansucrase that is derived from *Zymomonas mobilis* is useful in the present invention. For the effective catalysis of levan production, the enzyme is used at an amount of 0.42–3.0 U/ml based on the total volume of the reaction solution, and preferably at an amount of 2.08 U/ml.

Usually, gene manipulation leads to the mass production of proteins, which is very advantageous in purification. Thus, the levansucrase of the present invention is preferably obtained through genetic recombination. To this end, first, a plasmid carrying a *Z. mobilis*-derived levansucrase gene, e.g., the plasmid pZL8 obtained from *E. coli* KCTC 8546P, is used as a template to amplify the levansucrase gene by the polymerase chain reaction (PCR) with appropriate synthetic primers. Subsequently, the amplified gene of interest is inserted in a vector which is able to be expressed in a suitable host. For instance, when *E. coli* is used as a host, the levansucrase gene amplified is inserted in pET3d (Stratagene) to construct an *E. coli*-expression plasmid, e.g., pEL11 which is then transformed into the host. This transformed host cell is cultured under an appropriate condition and homogenized, followed by centrifugation. To the supernatant, ammonium sulfate is added to give crude levansucrase.

Since the crude enzyme contains various proteins in addition to levansucrase, a complicated purification procedure is required to obtain pure levansucrase. In order to overcome this problem, there is provided a levansucrase further comprising histidine residues at its N- or C-terminus, which can be simply purified by metal ion-exchange column chromatography, in accordance with the present invention.

Histidine residues can be attached to the N- or C-end of levansucrase as follows. First, PCR is conducted using a set of synthetic primers which are designed to have a histidine base sequence at their 3' or 5'-end while a plasmid carrying a *Z. mobilis*-derived levansucrase gene, e.g., the plasmid pZL8 obtained from *E. coli* KCTC 8546P is used as a template, so as to yield a large quantity of a levansucrase gene which further comprises a nucleotide sequence coding histidine at its 3' or 5'-end. Thereafter, the amplified gene is inserted in a vector which is expressable in a suitable host. For instance, when *E. coli* is used as a host, the levansucrase gene amplified is inserted in pET3d to construct an *E. coli*-expression plasmid, e.g., pEL11 which is then transformed into the host. This transformed host cell is cultured under an appropriate condition and homogenized, followed by purification with metal ion-exchange column chromatography to obtain pure levansucrase.

Experimental data show that, when 0.5–2 U of the levansucrase purified is added in a 20% sugar solution, levan is produced at an amount of 50 g/l after 10 hours of the enzymatic reaction at 10° C.

By using the levansucrase, levan, a water-soluble, homopolysaccharide, can be mass-produced in a batch process or a continuous process at a high purity (≧98%) at a high yield (35–40% from sucrose). In the case of a batch process, because the activity of the levansucrase is inhibited by glucose, a product of the enzyme reaction, the concentration of the substrate must be controlled. Preferable is a 20% substrate solution. As for the continuous process, there is needed a reactor, e.g., a membrane bioreactor, equipped with a means of continuously removing the glucose produced.

After the production of levan, to discard the enzyme used is too extravagant. In this regard, the enzyme may be immobilized to a suitable matrix, such as hydroxyapatite, iron-bead, non-porous glass, wire, etc. in order to reuse the enzyme.

In addition to being a substrate for producing DFA IV, the levan produced according to the present invention, as aforementioned, can be used for various purposes, such as a material for foodstuffs and medicines.

2. Purification and Concentration Process of Levan

After completion of the enzymatic production reaction of levan, the resulting levan-containing solution must be deprived of unreacted residual sucrose, glucose, and oligosaccharides, followed by concentration preferably by as much as 10–15%. To this end, available are various techniques, such as solvent precipitation, ultrafiltration, diafiltration, reverse osmosis, chromatography, etc. For a small scale, such as a laboratory scale, an organic solvent method using, for example, ethanol is suitable. Only to precipitate twice or three times in the organic solvent is sufficient to obtain pure levan. For a large scale, a membrane filtration process is preferably employed, as in various polymer production processes.

Where the levan is produced in a continuous process, membrane isolation techniques, such as microfiltration (MF), ultrafiltration (UF) or reverse osmosis (RO), are used to effectively isolate the product of interest or remove by-products from the reaction solution. These techniques have advantages of being able to be operated at low temperatures as well as allow the simple measurement of energy yield and separation capacity. For example, the glucose can be removed from the reaction mixture with the aid of ultrafiltration (UHF-500-E-90A, 500,000 molecular weight cutoff, A/G Technology Co.) or MF (CPP-1-k-9A, 0.1 microl, A/G Technology co.). Preferred is UHF-500-E-90A, which is superior in permeate flux and permeability (permeate flux, 376.47 ml.$ft^2$; permeability, 21.16 ml/min/$ft^2$/psi; 500,000 nominal molecular weight cutoff)

To achieve excellent purification of the levan, the filtration described above may be used in combination with the organic solvent precipitation. Alternatively, the purification of the levan may be accomplished by conducting various membrane isolation techniques in multiple steps.

3. DFA IV Production Process by Levan Fructotransferase

In accordance with the present invention, DFA IV is produced from partially purified or pure levan by the catalysis of levan fructotransferase.

In the presence of the levan fructotransferase, levan is subjected to reaction at 25–50° C. and preferably at 37° C. for a time period of 3–10 hours and preferably for 5 hours in a buffer of pH 3.0–7.0 and preferably of pH 5.8. Preferable is a phosphate buffer.

Useful to produce difructose dianhydride is partially or completely purified levan with preference to completely purified levan.

In the reaction solution, the levan is preferably controlled to have a concentration of 5–15% (w/v) based on the total volume of the culture and most preferably 10% (w/v).

Regardless of whether it is natural or is made by genetic recombination from transformable microbes such as *E. coli* or yeasts, the levan fructotransferase that is derived from *A. ureafaciens* is useful in the present invention.

The levan fructotransferase of the present invention is preferably obtained through genetic recombination because gene manipulation leads to the mass production of the protein, which is very advantageous in purification. To this end, first, a plasmid carrying an *A. ureafaciens*-derived levan fructotransferase gene, e.g., the plasmid pDA18, is used as a template to amplify the levan fructotransferase gene by PCR with appropriate synthetic primers. Subsequently, the amplified gene of interest is inserted in a vector which is able to be expressed in a suitable host, such as bacteria or yeast.

In accordance with the present invention, the levan fructotransferase gene amplified is inserted in pUC18 to construct an *E. coli*-expression plasmid pUDFA18, which is then transformed into *E. coli* DH5α. The new bacterial cell thus obtained was named *E. coli* JUD81 and deposited in Korean Collection for Type Cultures, Korean Research Institute of Bioscience and Biotechnology on Sep. 1, 1999 at accession No. KCTC 8961P. The original deposit was converted to a deposit under the Budapest Treaty on Oct. 19, 2000 at accession No. KCTC 0877BP. This transformed host cell is cultured under an appropriate condition and homogenized, followed by centrifugation. Addition of ammonium sulfate to the supernatant allows the production of crude levan fructotransferase.

Since the crude enzyme contains not only levan fructotransferase, but also various other proteins, the crude enzyme must undergo a complicated purification procedure to obtain only levan fructotransferase. In order to overcome this problem, there is provided a levan fructotransferase further comprising histidine residues at its N- or C-terminus, which can be simply purified by metal ion-exchange column chromatography, in accordance with the present invention.

Histidine residues can be attached to the N- or C-end of levan fructotransferase as follows. First, PCR is conducted using a set of synthetic primers which are designed to have a histidine base sequence at their 3' or 5'-end while a plasmid carrying an *A. ureafaciens*-derived levan fructotransferase gene, e.g., the plasmid pUDFA18 obtained from *E. coli* KCTC 0877BP is used as a template, so as to yield a large quantity of a levan fructotransferase gene which further comprises a nucleotide sequence coding histidine at its 3' or 5'-end. Thereafter, the amplified gene is inserted in a vector which is expressable in a suitable host. For instance, when *E. coli* is used as a host, the levan fructotransferase gene amplified is inserted in pUC18 to construct an *E. coli*-expression plasmid, e.g., pUDFA18 with which the host is then transformed. This transformed host cell is cultured under an appropriate condition and homogenized, followed by the purification with metal ion-exchange column chromatography to isolate the levan fructotransferase comprising histidine residues at its N- or C-terminus.

Like levan, DFA IV can be mass-produced in a batch process or a continuous process by using the levan fructotransferase. This enzyme is also immobilized to a suitable matrix, such as hydroxyapatite, iron-bead, non-porous glass, wire, etc. in order to reuse the enzyme.

Experimental data show that, when 20 g of the levan produced by the catalysis of the levansucrase of *Z. mobilis* was allowed to react with a homogenized cell solution containing 25 U of the levan fructotransferase at 37° C. in 1000 ml of a phosphate buffer (pH 5.8), DFA IV was produced at a yield of 60% after 20 hours of the reaction.

4. DFA IV Recovery Process by Crystallization

From the levan produced by the catalysis of the levansucrase of *Z. mobilis,* a reaction solution comprising DFA IV 60%, fructose 5%, limited levan 30%, and other saccharides (mainly, oligosaccharides) 5% is obtained as a result of the decomposition activity of the levan fructotransferase. This reaction solution is subjected to a purification process to isolate DFA IV, or concentrated to some degree to give a solution with a high content of DFA IV. If necessary, the reaction solution itself may be used instead of DFA IV.

Isolation of DFA IV from the resulting reaction solution may be achieved by conducting crystallization, solvent precipitation, diafiltration, ultrafiltration, reverse osmosis, evaporation, drying, chromatography, etc., alone or in combination. Useful in the present invention is a membrane filtration, which is usually used in various polymer production processes, in practice.

In addition to being more stable to heat than sucrose, DFA IV well crystallizes. For the purpose of crystallizing DFA IV, the enzymolyzed solution of levan needs to be concentrated. In this connection, the above-mentioned filtration processes or a popularized standard sugar solution evaporation process may be utilized. Alternatively, the enzymolyzed solution may be primarily concentrated to some degree by filtration and then, heated at 70–80° C. until DFA IV reaches a desirable concentration. At this time, a heating temperature exceeding 100° C. causes caramelization. The DFA IV filtrate of the primary filtration may be used as a diluting solution of the levan.

In a small scale site, such as a laboratory, the DFA IV solution is preferably added with two volumes of an organic solvent, such as ethanol, to precipitate oligosaccharides or limited levan and the resulting supernatant is concentrated using a rotary evaporator, after which the concentrate is controlled to an ethanol concentration of 95% with 100% ethanol and allowed to stand at 4° C. to induce crystal precipitation. Alternatively, while a supersaturated solution of DFA IV is allowed to stand at 4° C. to induce natural crystallization, DFA IV crystals are seeded to rapidly form crystals. These batch crystallization processes are, however, disadvantageous in that it is difficult to obtain uniform crystals. In contrast, a continuous process is very useful in crystallizing DFA IV at a uniform size and shape as well as has an advantage of being of low cost compared with the batch process.

A better understanding of the present invention may be obtained in light of the following examples which are set forth to illustrate, but are not to be construed to limit the present invention.

EXAMPLE

Experimental Example 1

Cloning of Levansucrase Gene

The isolation of genomic DNA from *Z. mobilis* was executed according to the instruction of Raymond and Tate (Raymond and Tate, Recombinant DNA techniques, p.162, 1983, Addison-Wesley Publ.). After being washed with a TEN buffer (10 mM Tris-Cl pH 7.6, 1 mM EDTA, 10 mM NaCl), 1 g of a mass of *Zymomonas mobilis* ZM1 (ATCC 10988) which had been cultured in a YPS medium (Yeast extract 0.5%, peptone 1%, sucrose 2%) was suspended in 10 ml of an SET buffer (sucrose 20%, 50 mM Tris-Cl pH 7.6, 50 mM EDTA) and treated with lysozyme (Sigma, 5 mg/ml PEN buffer). After 30 min of the enzyme treatment, the mixture was added with 10 ml of a TEN buffer and 1 ml of 10% sodium dodecylsulfate (SDS) and slowly agitated. To the lysed cells was added 2 ml of a 5 M NaCl solution and 20 ml of a TEN buffer and the resulting solution was added with an equal volume of a phenol solution saturated with a TE buffer (10 mM Tris-HCl pH 7.6, 1 mM EDTA) and agitated for 5 min, followed by centrifugation at 10,000 rpm for 5 min. The supernatant was further centrifuged after being well mixed with chloroform/n-amyl alcohol (24:1). Addition of two volumes of cold ethanol to the resulting supernatant precipitated DNA.

After purification, the *Z. mobilis* genomic DNA was partially cut with the restriction enzyme Sau3AI and DNA fragments in a size range of 4–10 kb were isolated with the aid of 1% agarose gel. Separately, pUC119 (Takara, Japan) was cut with the restriction enzyme BamHI and dephosphorylated. Recombinant plasmids were obtained by ligating the isolated DNA fragments of 4–10 kb to digested pUC 119.

Following the techniques of Mandel and Higa (Mandel and Higa, J. Mol. Biol. 53, 159 (1970)) and Inoue et al. (Inoue et al., Gene 96, 23 (1990)), transformation was executed. First, *E. coli* JM109 that had been cultured at 18° C. for 36 hours in 30 ml of an SOB medium (Trypton 2%, Yeast extract 0.5%, 10 mM NaCl, 2.5 mM $CaCl_2$, 10 mM $MgCl_2$, 10 mM $MgSO_4$) was kept in ice for 10 min and centrifuged at 2500×g for 10 min, after which the cell pellet was suspended in 10 ml of a TB solution (10 mM PIPES, 55 mM $MnCl_2$, 250 mM KCl). The resulting suspension was added with dimethyl sulfoxide (DMSO) to the final concentration of 7%, kept in ice for 10 min, aliquoted at 400 μl in cold tubes, and stored in a liquid nitrogen tank. For transformation, the frozen cell suspension was thawed at room temperature and well mixed with 10 μl of the recombinant DNA (DNA 1 μg) and this mixture was refrigerated for 30 min and subjected to heat-shock at 42° C. for 30 sec. Subsequently, the transformation solution was added with 800 μl of an SOC medium (Trypton 2%, Yeast extract 0.5%, 10 mM NaCl, 2.5 mM $CaCl_2$, 10 mM $MgCl_2$, 10 mM $MgSO_4$, 10 mM Glucose), vigorously shaken at 37° C. for 1 hour, spread over the surface of an LB agar plate containing ampicillin and chloramphenicol, and cultured at 37° C. for 16 hours.

The colonies formed were transferred to an MG agar plate supplemented with sucrose (20 g/l) and ampicillin (50 mg/ml) and cultured at 37° C. for 2 days. Spraying GOD-PAP (Böeringer Mannheim) onto the plate allowed the selection of 13 colonies which formed red halos around themselves. Further selection was on the colonies which could be of sucrase activity as well as of levan formativity as measured according to the instruction of Gay et al. (Gay et al., J. Bacteriol. 153, 1432(1983)). From the *E. Coli* colonies, plasmids were isolated and named "pZL8". *E. coli* DH5α bearing the plasmid was deposited in Korean Collection for Type Cultures, Korean Research Institute of Bioscience and Biotechnology on Dec. 14, 1993 at deposition No. KCTC 8546P.

Gene Identification by Levan Formation

Cultivation of the *E. coli* bearing pZL8 at 37° C. for 3 days in an LBS broth (LB broth supplemented with sucrose at 5%) resulted in the detection of polymers similar to those of levan. The culture was centrifuged and the supernatant was added with three volumes of cold ethanol to precipitate polymers. They were dissolved in distilled water and precipitated with ethanol. This ethanol precipitation procedure was carried out twice more. The raw polymers thus obtained were separated by thin layer chromatography (TLC) on silica gel developing with n-butanol/pyridine/water (8/1/1), followed by the coloration with a 1% anisaldehyde-sulfuric acid solution.

Because levan, a macro-molecule with a molecular weight of $5\times10^7$ Daltons, cannot move on TLC, it was hydrolyzed according to the instruction of Tanaka (Tanaka et al., J. Biochem. 90, 521 (1981)). 100 μl of the raw polymer solution was boiled for 15 min, along with 50 μl of 2.5% oxalic acid, and the hydrolyzed solution was subjected to TLC. The acid hydrolysate was extended for 15 min, only fructose was observed. There were difficulties in analyzing the sugar components with accuracy by TLC because the Rf value was 0.46 for glucose, 0.52 for fructose, and 0.4 for sucrose. To compensate for this, HPLC analysis was executed.

20 μl of each of the hydrolysate samples was filtered through a 0.2 μm membrane and subjected to HPLC with the aid of an HPLC apparatus, such as sold by Waters, identified as "Model R401", by flowing water at a rate of 0.6 ml/min through a column carbohydrate HPX-87C (Bio-Rad). Detection was conducted using RI (Oven Temp. 85–90° C.). All of the samples showed two peaks: a peak was read at 4.19 min for oxalic acid and the other peak at 9.29 min for sucrose. These data, therefore, demonstrated that the polymer obtained above was composed of fructose residues. In addition, no inulin (β(2-1) linked polyfructan) formative activity was observed in *Z. mobilis* (Toran et al., *J. Biotechnol. Lett.* 7, 527(1985)). Consequently, it was made certain that the polymers formed in the *E. coli* bacteria bearing the plasmid pZL8 were levan (β(2-6) linked polyfructan) (Viikari, L., *CRC Critical Reviews in Biotechnology* 7, 237 (1988)) and a levansucrase gene was introduced in the plasmid pZL8.

Gene Identification by Gene Mapping

The recombinant plasmid obtained above was digested with various restriction enzymes and electrophoresed on 1% agarose gel. Based on the DNA fragment data on the agarose gel, a restriction enzyme map of the plasmid pZL8 was drawn, providing the information that the genomic DNA introduced in the plasmid pZL8 was 4.5 kb long.

To be used as a probe, the plasmid pZL8 was labeled with a DNA labeling kit (Böeringer Mannheim). Separately, the Zymomonas mobilis genomic DNA prepared above was cut with Restriction enzymes, EcoRI, EcoRV, HindIII and NcoI and electrophoresed on 1% agarose gel. Then, the genomic DNA fragments on the agarose gel were transferred to a nylon membrane and hybridized with the probe in accordance with the teaching of Southern (Southern, *J. Mol. Biol.,* 98, 503 (1975)). Referring to the instruction enclosed in the DNA labeling kit, coloration was achieved; Because the plasmid pZL8 has a unique restriction enzyme site for each of EcoRV, HindIII and NcoI, the DNA sequence of 4.5 kb introduced into the plasmid pZL8 must be from *Z. mobilis.*

Gene Identification by Base Sequencing

Figure 2:
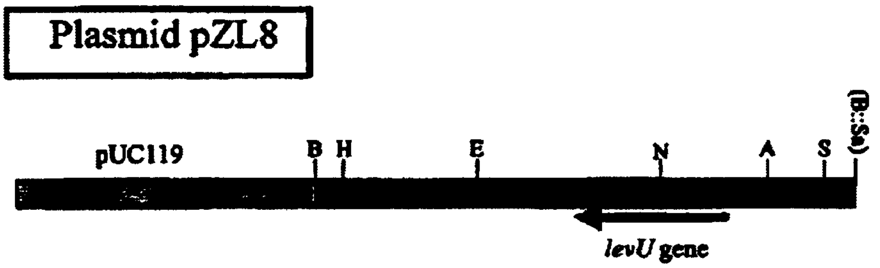
FIG. 2 shows the restriction map of plasmid pZL8, in which B stand for BamHI, H for HindIII, E for EcoRV, N for NcoI, A for AseI, S for SphI, (B::Sa) for BamHI::Sau3A1.

An examination was made of the levansucrase activity of the mutant bacteria bearing delete pZL8 which was made by use of restriction enzymes. From the examination, it was recognized that the levansucrase gene was positioned in the 1.6 kb base sequence between the EcoRV site and the AseI site, as shown in FIG. 2.

Delete plasmids, which were constructed from the 1.6 kb DNA fragments with the aid of an exo/Mungbean delete kit (Takara, Japan), were amplified. 2 μl of the prepared plasmids prepared from the mutant cells was denatured with 2 N NaOH, neutralized with ammonium acetate (pH 4.5), allowed to precipitate by ethanol, and dissolved in deionized water. Using a Sequenase kit (USB, U.S.A.), the denatured plasmids were labeled and 4 μl of the reaction was boiled for 3 min and electrophoresed on 8% polyacrylamide-8M urea gel at 1500–1700 V for 3 hours. The gel was dried and exposed to X-ray film at −70° C. for about 8 hours. The reading of the base sequence which appeared on the sensitized X-ray film revealed that the total levansucrase gene including its one termination codon is 1800 bp long: the structural gene corresponding to the amino acid sequence is 1269 bp long. The base sequence of the levansucrase gene and the amino acid sequence deduced therefrom are as shown in FIG. 3.

Gene Identification by Amino Acid Sequencing *Z. mobilis* ZM1 was cultured at 30° C. for 24 hours in a YPS medium and the multiplied cells were harvested, suspended in a 20 mM phosphate buffer (pH 6.8), shaken at 30° C. for 15 min, and centrifuged according to the introduction of Yanase (Yanase et al., *Biosci. Biotech. Biochem.* 56, 1335 (1992)). The supernatant was used as a crude enzyme solution.

In this crude solution, ammonium sulfate was saturated up to 50%, to precipitate proteins which were recovered by centrifugation at 8,000×g for 20 min. The protein mass was dissolved in a 0.02 M phosphate buffer (pH 6.8), followed by dialysis in the same buffer. In this regard, elution was conducted at a rate of 0.5 ml/min through a column (2.5×10 cm) charged with a weak anion exchange resin (DEAE-Toyopearl 650M). In a linear concentration gradient of NaCl from 0 to 0.5 M, the eluate at 0.3 M was collected. The eluate was concentrated and purified followed by Hydroxyapatite column chromatography. After being concentrated, The protein was allowed to precipitate with 20% saturated ammonium sulfate. And finally the concentrate was loaded on a gel filtration column (Superose 12, Pharmacia) to elute a fraction containing a molecular weight of 91,000. The final purification yield was 18.3 fold of the crude enzyme from *Z. mobilis,* with 16.5% of the enzyme recovered in the preparation step (Table 1). The solution was used as a levansucrase solution.

TABLE 1

Summary of levansucrase purification steps from *Z. mobilis*

| Step | Volume (ml) | U total | Protein (mg/ml) | Spec. Act. (U/mg) | Yield (%) | Purifi. Fold |
|---|---|---|---|---|---|---|
| Cell washed | 1,300 | -a | 0.35 | — | — | — |
| 1st $(NH_4)_2SO_4$ | 115 | — | 1.28 | — | — | — |
| Ion-exchange | 38 | 4.35 | 0.57 | 0.21 | 100 | 1.00 |
| Hydroxyapatite | 20 | 2.58 | 0.41 | 0.31 | 65 | 1.52 |
| 2nd $(NH_4)_2SO_4$ | 2 | 0.96 | 0.46 | 1.04 | 21 | 5.07 |
| Superose 12 | 1.5 | 0.72 | 0.13 | 3.75 | 16.5 | 18.3 |

a: could not be determined.

With the aid of a protein-peptide sequencing system (Applied Biosystems, Model 477A), the amino acid sequence of the purified levansucrase was determined at its N-terminal in the Edman degradation procedure. As a result, a stretch of seven amino acid residues, Met-Leu-Asn-Lys-Ala-Gly-Ile, was sequenced, reflecting the corresponding base sequence of the DNA. In particular, the levU gene was revealed to have no base sequences which correspond to the signal peptides, which are usually found in secretory proteins. The nucleotide and amino acid sequences of the levansucrase gene from *Z. mobilis* was registered in the GenBank, U.S.A. (Accession No. AF081588).

Experimental Example 2

Production of Levansucrase

Step 1 Construction of Expression Vector

*E. coli* KCTC 8546P was cultured at 37° C. overnight in an LB medium (yeast extract 0.5%, trypton 1%, NaCl 1%), after which plasmid pZL8 was extracted from the culture, according to the method of Maniatis et al. (Maniatis et al., *Molecular Cloning: A Laboratory manual,* 2nd ed., Cold Spring Harbor Laboratory, Cold Spring Harbor, N.Y., U.S.A.).

A levansucrase gene 1296 bp long was amplified by a PCR which employed two primers with the plasmid pZL 8 serving as a template.

A reaction mixture comprising a 10×Taq polymerase buffer (10 ul), a 10×dNTP mix (10 ul) (dATP, dCTP, dGTP, and dTTP, 2 mM each), the primers 1 and 2 (1 ul (100 pM), each), the plasmid pZL8 DNA (5 ul (20 ng)), and deionized water (72 ul) was thermally treated, along with a mineral oil (100 ul), at 95° C. for 5 min to denature the DNA. The reaction mixture was added with a Taq polymerase (1 ul (5 U)) after being cooled to 72° C. and then, allowed to undergo 25 thermal cycles in which heating processes were performed in the order of at 95° C. for 1 min, at 55° C. for 2 min and at 72° C. for 3 min.

The PCR product thus obtained was digested with the restriction enzyme AflIII and introduced into the NcoI site of the plasmid pET3d (Stratagene) to construct the *E. coli*-expression plasmid pEL11.

Step 2 Transformation of *E. coli*

*E. coli* DH5α and BL21 (DE3) were separately cultured at 18° C. for 36 hours in 30 ml of an SOB medium (Trypton 2%, Yeast extract 0.5%, NaCl 10 mM, calcium chloride 2.5 mM, magnesium chloride 10 mM, magnesium sulfate 10 mM), followed by centrifugation to harvest the bacteria. Subsequently, the cultured bacteria were separately suspended in 10 ml of a TB buffer (Pipes 10 mM, manganese chloride 55 mM, calcium chloride 15 mM, potassium chloride 250 mM), followed by centrifugation to collect the cells. The cell mass was resuspended in 12 ml of a TB buffer and after being added with DMSO (dimethyl sulfoxide) at a concentration of 7%, the suspension was kept on ice and stored at an aliquot of 400 ul in a liquid nitrogen tank.

After being thawed, the *E. coli* DH5α was added with 10 ul of the plasmid pEL11 constructed in the Step 1 and kept on ice for 30 min, followed by heat shock at 42° C. for 30 sec for transformation. The transformed cell mixture was added with 800 ul of an SOC medium, vigorously agitated at 37° C. for 60 min, and spread on an LB agar containing 170 mg/ml of ampicillin, which was then incubated at 37° C. for 16 hours. Colonies formed on the agar medium were taken and cultured in LB broths containing ampicillin. Plasmids were extracted from the cells cultured and tested for whether they carried the levansucrase gene, by restriction enzyme mapping.

*E. coli* BL21 (DE3) was transformed by the recombinant plasmid which had been ascertained to carry the levansucrase gene, spread on an ampicillin-added LB agar, and incubated at 37° C.

Step 3 Production and Isolation of Levansucrase

The transformed cells were inoculated in M9-ZB media (Trypton 10 g, NaCl 5 g, $NH_4Cl$ 1 g, $KH_2PO_4$ 3 g, $Na_2HPO_4$ 6 g, Glucose 4 g, 1 M $MgSO_4$1 ml) and cultured with agitating. When the absorbance at 600 nm of the culture reached 0.7 during the cultivation, IPTG (Sigma) was added to the concentration of 1 mM with the aim of inducing the expression of the levansucrase.

To the cell pellet which was obtained by centrifuging the culture, a 100 mM Tris buffer (pH 7.0) was added at an amount of 1/10 volume of the culture, and the suspended cells were homogenated by sonicating three times for 30 sec with the aid of a sonifier (Branson), followed by centrifugation at 12000×g for 60 min. The supernatant thus obtained was added with ammonium sulfate to the concentration of 20% and centrifuged to give above 94%-pure levansucrase. This crude enzyme mass was found to have a levansucrase activity of 7.8 U/ml, if harvested at 4 hours after the IPTG induction, as measured according to the instruction described in Song et al. (song and Rhee, *Biotechnol. Lett.* 16, 1305 (1994)) Example 2. It amounted to 30% of the total quantity of the proteins produced from the *E. coli.*

Comparative Example 1

*Z. mobilis* ATCC 10988 was cultured in a YPS medium (Yeast extract 1%, potassium phosphate 0.1%, sucrose 20%) at 30° C. for 18 hours, and from the culture was obtained levansucrase which was measured to have an activity of 1.5 U/ml.

Therefore, the amount of the levansucrase produced from the transformed cells in Experimental Example 2 was 5.2 times as much as that of the levansucrase produced from *Z. mobilis* ATCC 10988.

Example 1

While *E. coli* was cultured as in the Step 3 of Experimental Example 2, the culture was taken out at 10 ml at regular intervals of time, and centrifuged. To the cell pellet was added a 100 mM Tris buffer (pH 7.0) at an amount of 1/10 volume of the culture, and the suspended cells were homogenated by sonicating three times for 30 sec with the aid of a sonifier, followed by centrifugation at 12000×g for 60 min. The supernatants were electrophoresed on a 10% polyacrylamide gel.

The polyacrylamide gel electrophoresis showed that the levansucrase was water-soluble by 6 hours after the IPTG induction and was gradually converted into a water-insoluble one from 8 hours after the IPTG induction with a gradual decrease in enzyme activity. At 10 hours after the IPTG induction, the levansucrase was measured to have an enzyme activity of 10%.

Example 2

A PCR was carried out using two primers while the plasmid pZL8 isolated from *E. coli* KCTC 8546P served as a template. Using the PCR product, the same procedure as Experimental Example 2 was repeated to construct the plasmid pEL12 capable of expressing the levansucrase carrying histidine residues at its C-terminus in *E. coli,* which was then used for the transformation of *E. coli* BL21 (DE3).

The transformed *E. coli* BL21 (DE3)/pEL12 was deposited in Korean Collection for Type Cultures, Korean Research Institute of Bioscience and Biotechnology on Apr. 25, 1995 at deposition No. KCTC 8861P.

Example 3

Ni-NTA resin (Quagen, U.S.A.) was charged in a 1.5×20 cm column through which a 50 mM phosphate buffer (pH 8.0) was then flowed to give a column for metal ion-affinitive chromatography.

Figure 4:
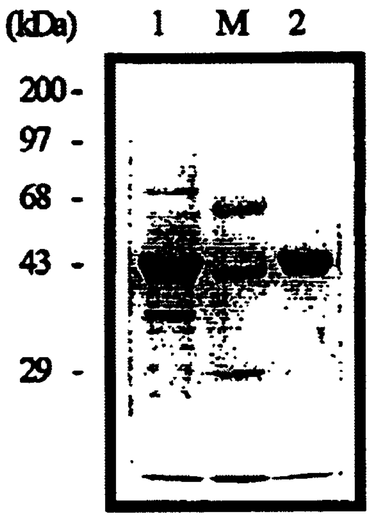
FIG. 4 shows a SDS-PAGE result of purified levansucrase, in which a standard protein is electrophoresed in lane M, total protein of *E. coli* in lane 1 and the purified levansucrase in lane 2.

*E. coli* KCTC 8861P of Example 2 was cultured in the same manner as the Step 3 of Example 1 and sonicated. The cell homogenate was loaded on the column which was then washed with a buffer (50 mM sodium phosphate, 300 mM NaCl, 10% glycerol, pH 6.0), followed by detaching the enzyme from the resin by flowing a 0.3 N imidazole solution (pH 7.0). The result is given in FIG. 4. As shown in FIG. 4, the enzyme was purified with above 95% of homogeneity (lane 2), from the total protein of *E. coli* lysate(lane 1).

Example 4

Using the levansucrase carrying histidine residues at its C-terminal, obtained in Example 3, the experimental procedures of Examples 3 to 8 were repeated. The data demonstrate that the recombinant levansucrase to the C-end of which histidine residues were attached, has levan production ability almost identical to that of natural levansucrase.

Experimental Example 3

Levan Production

In 5 ml of 50 mM acetic acid buffers which were controlled to pH 3–7.5, sucrose was dissolved to the concentration of 10%, followed by the addition of 0.42 U of the crude enzyme obtained in Experimental Example 2. The resulting mixture was allowed to react at 10° C. for 5 hours and 48 hours, after which a measurement was made of the amount of the levan produced.

The results are given in Table 2, below. As apparent from the data, levan was produced in the largest quantity when the buffer was pH 5.

TABLE 2

| Production Amounts of Levan According to pH of Buffer (g/l) | | | | | | | | | | |
|---|---|---|---|---|---|---|---|---|---|---|
| | PH | | | | | | | | | |
| Temp. | 3 | 3.5 | 4 | 4.5 | 5 | 5.5 | 6 | 6.5 | 7 | 7.5 |
| 5 | 6.6 | 8.0 | 9.3 | 10.0 | 10.5 | 9.2 | 7.0 | 5.5 | 4.3 | 3.0 |
| 48 | 26.7 | 30.0 | 32.9 | 35.2 | 35.9 | 31.1 | 28.0 | 27.5 | 22.1 | 17.1 |

Example 5

In 10 ml of a 50 mM acetic acid buffer (pH 5.0) was dissolved sucrose to the concentration of 10% and was added 1.05 U of the crude enzyme obtained in Experimental Example 2. The resulting mixture was allowed to react at −3° C., 0° C., 5° C., and 10° C. for up to 200 hours, after which a measurement was made of the amounts of the levan produced according to the condition parameters.

The results are given in Table 3, below. As apparent from the data, a reaction temperature of 10° C. was the best condition for the crude enzyme to produce levan until 50 hours of the reaction.

TABLE 3

| Production Amounts of Levan According to Reaction Temp. (g/l) | | | | | | |
|---|---|---|---|---|---|---|
| | Time period | | | | | |
| Temp. | 4 | 10 | 27 | 46 | 78 | 167 |
| −3° C. | 7.3 | 10.5 | 20.5 | 30.0 | 34.5 | 30.5 |
| 0° C. | 10.1 | 15.7 | 29.5 | 36.5 | 37.2 | 32.3 |
| 5° C. | 11.3 | 22.2 | 33.2 | 36.4 | 38.4 | 33.0 |
| 10° C. | 15.2 | 29.3 | 34.9 | 36.7 | 37.5 | 29.7 |

Example 6

In 10 ml of a 50 mM acetic acid buffer (pH 5.0) was dissolved sucrose to the concentrations of 5–40% and was added 2.08 U of the crude enzyme prepared in Experimental Example 2. The resulting mixture was allowed to react at 10° C. for up to 60 hours, after which a measurement was made of the amounts of the levan produced according to the condition parameters.

The results are given in Table 4, below. As apparent from the data, the levan amounts produced in a sucrose concentration of 30% were greater than in any other sucrose concentration.

TABLE 4

| Production Amounts of Levan According to Sucrose Concentration (g/l) | | | | | | |
|---|---|---|---|---|---|---|
| Sucrose | Time period | | | | | |
| Concentration | 2 | 11 | 18 | 25 | 36 | 59 |
| 5 | 12.1 | 19.0 | 21.8 | 21.6 | 21.4 | 20.8 |
| 10 | 14.8 | 38.2 | 36.7 | 39.1 | 34.2 | 34.9 |
| 20 | 14.1 | 51.4 | 56.7 | 52.9 | 51.4 | 52.0 |
| 30 | 14.6 | 52.4 | 71.1 | 66.9 | 69.8 | 59.4 |
| 40 | 11.5 | 39.1 | 59.8 | 58.8 | 60.0 | 56.4 |

Example 7

In 5 ml of a 50 mM acetic acid buffer (pH 5.0) was dissolved sucrose to the concentration of 10% and were added 0.42 U, 1.05 U, and 2.08 U of the crude enzyme prepared in Experimental Example 2. The resulting mixtures were allowed to react at 10° C. for up to 150 hours, after which a measurement was made of the amounts of the levan produced according to the condition parameters.

The results are given in Table 5, below. It is apparent from the data that the levan is produced at larger amounts by the greater activity of the enzyme.

TABLE 5

| Production Amounts of Levan According to Enzyme Concentration (g/l) | | | | | |
|---|---|---|---|---|---|
| Enzyme | Time period | | | | |
| Concentration | 4 | 12 | 48 | 96 | 144 |
| 0.42 U | 2.5 | 4.0 | 21.7 | 35.7 | 39.0 |
| 10.5 U | 4.9 | 12.9 | 34.9 | 48.5 | 42.2 |
| 20.8 U | 24.9 | 44.9 | 49.0 | 49.2 | 46.2 |

Example 8

In 5 ml of a 50 mM acetic acid buffer (pH 5.0) was dissolved sucrose to the concentration of 20% and were added 2.08 U of the crude enzyme prepared in Experimental Example 2. The resulting mixtures were allowed to react at 10° C. for up to 36 hours, after which a measurement was made of the amounts of the levan and other saccharides produced according to the condition parameter.

The results are given in Table 6, below. It is apparent from the data that the levan is produced at larger amounts by the greater activity of the enzyme.

TABLE 6

| Production Amounts of Levan According to Reaction Time (g/l) | | | | | | |
|---|---|---|---|---|---|---|
| | Time period | | | | | |
| Saccharides | 0 | 6 | 11 | 18 | 25 | 36 |
| Levan | 0 | 28.3 | 51.4 | 56.7 | 52.9 | 51.4 |
| Residual Sucrose | 200 | 161 | 125 | 120 | 98 | 10 |
| Glucose | 0 | 237 | 36.0 | 50.4 | 74.6 | 104.8 |
| Fructose | 0 | 2.5 | 5.8 | 6.2 | 6.5 | 7.2 |

Example 9

In 10 ml of a 50 mM acetic acid buffer (pH 5.0) was dissolved raw sugar (DaeHan Sugar Co.) to the concentration of 20% and were added 1.05 U of the crude enzyme prepared in Experimental Example 2. The resulting mixtures were allowed to react at 10° C. for up to about 91 hours, after which a measurement was made of the amounts of the levan and other saccharides produced. Levan was produced at an amount of 12.5 g/l after 11 hours of the reaction, 25.0 g/l after 25 hours, and 45.8 g/l after 91 hours.

Experimental Example 4

Selection of Strains Containing Levan Fructotransferase Capable of Producing DFA IV from Levan Strains were selected from samples taken from soil in Korea. 0.5 grams of each of the soil samples was suspended in 9.5 ml of distilled water and the suspensions were successively diluted to 10-fold, 100-fold and 1000-fold. 200 ul of each of the dilutions was spread on the surface of a selective agar plate, and incubated at 30° C. for 72 hours in an incubator. The selective agar medium contained 0.5% (w/v) of levan as a major carbon source, along with 0.3% of $NaNO_3$, 0.05% of $MgSO_4$, 0.02% of $MnCl_2$, 0.1% of $K_2HPO_4$ and 1.5 agar/L. A solution of a predetermined amount of levan in water was passed through a 0.45 micron filter and the filtrate was mixed with the other nutrients before being added to a sterilized medium. After the incubation, colonies around which halos had been formed were primarily selected as being capable of decomposing levan.

Inocula picked from the primarily selected colonies were inoculated in selective broths, each containing levan as a major carbon source, and cultured at 30° C. for 72 hours in an incubator. Investigation was made into the growth of the strains inoculated and the metabolites resulting from the metabolism of levan through thin layer chromatography (TLC). Of the 250 strains primarily selected, 8 strains of microbes were found to produce difructose dianhydride. Finally, one strain which stably produced difructose from levan with high enzyme activity was selected and named "K2032".

Identification of Strain K2032

The identification of the selected strain K2032 was achieved by examining its biochemical characteristics and the composition and content of its fatty acids and quinones and comparing them with the database previously accumulated. Many experiments revealed that strain K2032 is Gram-variable and is able to utilize glucose, fructose, galactose, arabinose, mannitol, xylose, ribose, sorbitol, cellobiose, glycogen, sucrose, acetic acid, propionic acid, and salicin, but not rhamnose, malonate, adipic acid, N-acetyl glutamic acid, and adipic acid. As for its intracellular fatty acid composition, the bacteria comprises C15 anteiso/C17 anteiso/C16 iso at a ratio of 51% /14.5%/3.6% with C16/C14 being at a ratio of 17.8%/7.1%. As a result of the analysis of quinones, which are important components for the chemotaxamomy of microbes, the bacteria contained menaquionone MK-9($H_2$).

With the analysis results, the strain K2032 was identified as *Arthrobacter ureafaciens,* and thus, named *A. ureafaciens* K2032 (Table 7).

TABLE 7

Phenotypic and chemotaxonomic characteristics of strain K2032

| Gram reaction | variable (+ when young) |
|---|---|
| Acid from glucose | – |
| Nitrate reduction | – |
| Starch hydrolysis | – |
| Growth in 10% NaCl | – |
| Utilization of D-glucose, D-fructose, D-galactose, L-arabinose, D-mannitol, D-xylose, D-ribose D-sorbitol, cellobiose, glycogen, sucrose, acetic acid, propionic acid, salicin | + |
| Utilization of L-rhamnose, malonate, adipic acid, N-acetyl glutamic acid, L-serine | – |
| Cellular fatty acid; | |
| C15 anteiso/C17 anteiso/C16 iso | 51%/14.5%/3.6% |
| C16/C14 | 17.8%/7.1% |
| Major menaquinone | MK-9($H_2$) |

Experimental Example 5

Purification of Levan Fructotransferase from Arthrobacter

Figure 5:
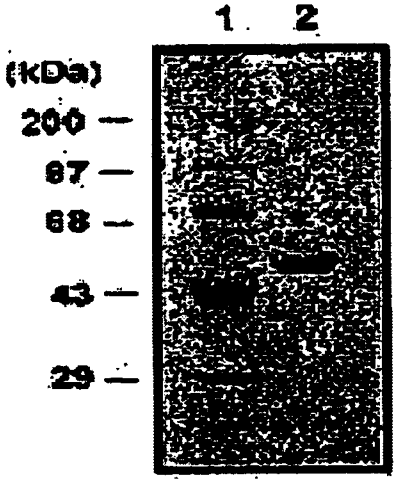
FIG. 5 shows a SDS-PAGE result of purified levan fructotransferase, in which a standard protein is electrophoresed in lane 1 and the purified levan fructotransferase in lane 2.

*A. ureafaciens* K2032 was inoculated in a selective broth containing levan as a major carbon source and cultured at 30° C. for 72 hours in an incubator. Investigation into the growth and levan fructotransferase activity of the bacteria provided the knowledge that the largest enzyme activity is obtained after 10 hours of the incubation. From the culture incubated for 10 hours, the enzyme was purified (FIG. 5). In this regard, the purification was achieved by successively using acetone precipitation, ion exchange chromatography (DEAE 650-M and Mono Q), and gel filtration chromatography, resulting in producing levan fructotransferase with a specific activity of 2269 U/mg protein at an amount of 1.1 mg at a yield of 29.8% (Table 8).

TABLE 8

Summary of levan fructotransferase purification from *A. ureafaciens* K2032.

| Purification step | Volume (ml) | Total activity (U) | Protein (mg) | Spec. Act. ($U\ mg^{-1}$) protein) | Purification Fold | Yield (%) |
|---|---|---|---|---|---|---|
| Culture supernatant | 3,800 | 8,360 | 182.3 | 45.9 | 1.0 | 100 |
| Acetone precipitation | 700 | 5,670 | 71.3 | 79.5 | 1.7 | 67.8 |
| Ion-exchange adsorption | 5.5 | 4,821 | 5.0 | 964.2 | 21.1 | 57.7 |
| $2^{nd}$ Ion-exchange adsorption | 3.2 | 3,416 | 2.6 | 1313.8 | 29.2 | 40.9 |
| Gel permeation (Superose 12) | 1.2 | 2,496 | 1.1 | 2269.0 | 49.8 | 29.8 |

Characterization of the Purified Enzyme

The purified enzyme was 51,000 in molecular weight as measured by SDS-PAGE while being measured to have a molecular weight of 96,000 by gel filtration chromatography. Thus, it was identified as being a dimer in aqueous conditions. An amino acid analysis showed the amino acid sequence of the C-terminus of the enzyme. Maintaining its stability in a pH range of 4–10.5, the enzyme showed optimal activity at around pH 6.0. Also, it was of optimal activity at 55° C. After being allowed to stand at 50° C. for 30 min, the enzyme was observed to have a remnant activity of 90% or greater (Table 9). Whereas being inhibited by $Mn^{2+}$, $Fe^{2+}$ and $Hg^{2+}$, the activity of the enzyme was enhanced by $Na^{2+}$ and $Ca^{2+}$.

TABLE 9

Effect of additives on the activity of levan fructotransferase from *A. ureafaciens* K2032

| Additive | Concentration (mM) | Relative activity (%) |
| --- | --- | --- |
| Control | — | 100 |
| NaCl | 1, 10 | 125, 142 |
| $NH_4Cl$ | 1 | 46 |
| $MnCl_2$ | 1 | 9 |
| $CaCl_2$ | 1, 10 | 156, 181 |
| NiCl | 1 | 74 |
| $ZnCl_2$ | 1 | 23 |
| LiCl | 1 | 92 |
| $MgCl_2$ | 1 | 63 |
| $FeCl_2$ | 1 | 4 |
| $HgCl_2$ | 1 | 0 |
| KCl | 1 | 89 |
| EDTA | 1, 10 | 95, 94 |
| SDS | 1, 10 | 101, 32 |

Experimental Example 6

Isolation of Genomic DNA from Arthrobacter

Isolation of a gene coding for a levan fructotransferase from *A. ureafaciens* was performed using a genome DNA isolation kit, such as that sold by Bio 101, identified as "G NOME™ DNA ISOLATION KIT", according to its instruction. First, *A. ureafaciens* K2032 was inoculated in 50 ml of a selective broth and cultured for 24 hours, followed by centrifugation at 3,000 rpm for 5 min to harvest cells. To the cell pellet was added the cell suspension solution (10 mM Tris-HCl (pH 8.0), 0.1 M EDTA (pH 8.0)) to the volume of 1.85 ml. This cell suspension was well mixed with 100 ul of the cell lysis/denaturing solution (0.5% SDS), along with 50 ul of the RNase solution, and incubated at 55° C. for 15 min. To remove proteins from the sample, 25 ul of the protease was added and incubated at 55° C. for 1 hour. After 500 ul of the salt out solution was added, the mixture was aliquoted in 1.5 ml tubes which were then cooled at 4° C. for 10 min. Following centrifugation at 12000 rpm for 10 min, the supernatant was transferred to a 15 ml tube, in which 2 ml of TE buffer and 8 ml of 100% ethanol were added to induce DNA precipitation. The DNA precipitates were collected by centrifugation at 12,000 rpm for 15 min, dried in the air and dissolved in a TE buffer.

Cloning of Levan Fructotransferase-Coding Gene

The genome DNA prepared from *A. ureafaciens* was digested with various restriction enzymes and electrophoresed on 1% agarose gel, after which DNA fragments in a size range of 3–4 kb were eluted from the agarose gel. The partial genomic DNA fragments were ligated into the cloning vector pBluescript $KSII^+$ which was previously cut with BamHI. This recombinant plasmid was transformed into *E. coli* DH5α. Of the transformants, the cells carrying a gene coding for a levan fructotransferase were selected as follows.

First, a sequence in the N-terminal amino acid sequence of the K2032 strain and a second amino acid sequence, which was found to be in a homology relationship with levan fructotransferase, were used to synthesize degenerated primers. Using these primers, a standard PCR was carried out with the genomic DNA of K2032 bacteria serving as a template. The PCR products ranging, in size, from 600 to 650 bp were eluted from the gel and introduced into shuttle vectors for *E. coli.* As a result of restriction enzyme gene mapping, the DNA fragments introduced were identified as being divided into four kinds and the vectors carrying these DNA fragments were called pDA11, 17, 18 and c8, respectively. In addition, base sequencing analysis of the four DNA fragments showed that the DNA fragment inserted in pDA11 and the levan fructotransferase gene of *A. nicotinovorans* are in high homology (85%) relationship. Therefore, the DNA fragment introduced in pDA18 could be used as a probe for the Southern hybridization with the DNA prepared from *A. ureafaciens* K2032 with the aim of detecting the levan fructotransferase gene anchored in the bacteria. Before the Southern hybridization, the genomic DNA of *A. ureafaciens* K2032 was digested with various restriction enzymes. As a result of the Southern hybridization, a signal was detected in a 5.6 kb DNA fragment upon digestion with ClaI, in a 8.0 kb DNA fragment upon digestion with PstI, and a DNA fragment longer than 10 kb upon digestion with BamHI. Accordingly, the genomic DNA was cut with either ClaI or PstI and electrophoresed on a 1% agarose gel, after which DNA fragments in a size range of 5–10 kb were eluted from the agarose gel. The partial genomic DNA fragments were ligated into the cloning vector pBluescript $KSII^+$ which was previously cut with ClaI or PstI. These recombinant plasmids were transformed into *E. coli* DH5α. Of the transformants, the cells carrying a gene coding for a levan fructotransferase were selected by Southern hybridization. Finally, when cutting with ClaI, there was obtained plasmid pDC a carrying a 5.6 kb DNA fragment. On the other hand, when cutting with PstI, there was obtained plasmid pDpst carrying a 8.0 kb DNA fragment.

Isolation Analysis and Subcloning of the Recombinant Plasmids

DNA preparation from the transformed *E. coli* was carried out by an ordinary boiling method and with the aid of a commercially available kit. To analyze the recombinant plasmids, they were digested with restriction enzymes and electrophoresed on 1% agarose gel.

The restriction enzyme gene mapping of the DNA fragments introduced in pDcla and pDpst, the analysis of gene loci, and the Southern blotting with DNA fragments showed that pDcla and pDpst carried an N-terminal half and a C-terminal half of the gene of interest with an overlapping stretch of about 200 bp therebetween. No enzymatic activity was detected from the bacteria which anchored the two plasmids respectively. According to a base sequencing analysis, the sites for restriction enzymes PstI, ApaI and NotI were found to be present in both of the plasmids. By taking advantage of these common restriction enzyme sites, there was constructed plasmid pDF8 which has a complete open reading fame (ORF). A DNA fragment 3.5 kb long was introduced in the plasmid pDF8 and enzymatic activity was detected from the bacteria anchoring this plasmid.

Figure 6:
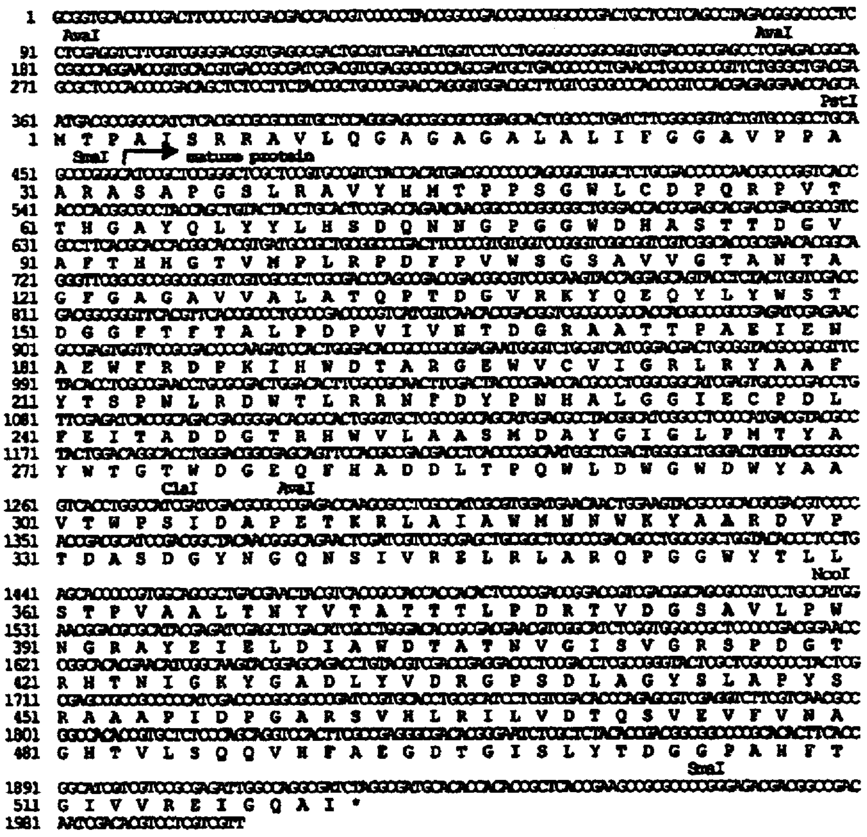
FIG. 6 shows a nucleotide base sequence of the levan fructotransferase gene (SEQ ID NO: 2) and an amino acid sequence (SEQ ID NO: 1) deduced therefrom, with translation start and restriction sites indicated.

Base Sequence of the Cloned Levan Fructotransferase Gene and Its Putative Amino Acid Sequence In order to analyze the nucleic acid base sequence of the 3.5 kb DNA introduced into pDF8, DNA ladder fragments which showed a regular distance of about 300–400 bp were made and subjected to a sequencing process. As a result, a sequence of 3345 bases was ascertained and found to have only one ORF. Using the BLAST search, which is available from the Internet, the ORF was investigated for homology. In result, a levan fructotransferase gene was detected as being high in the homology with the ORF, and thus, it was named lftA. FIG. 6 shows the base sequence of lftA and the amino acid sequence deduced therefrom.

The newly isolated levan fructotransferase structural gene is composed of 1566 bp which corresponds to 521 aa. The gene of the present invention has a signal sequence consisting of 99 bp (corresponding to 33 aa) at its N-terminus and therefore, the putative completed protein may be about 56 kDa in molecular weight. Its isoelectric point was found to be pH 5.15. This levan fructotransferase gene is longer by 15 bases (5 amino acids) than is the levan fructotransferase gene derived from *A. nicotinovorans* GS-9. These two genes are 81% in the homology of amino acid sequence (76% in the homology of base sequence). Consequently, the levan fructotransferase gene of *A. ureafaciens* K2032 was identified as being new and its base sequence was registered in the GenBank, U.S.A. (Accession No. AF181254).

Experimental Example 7

Figure 7:
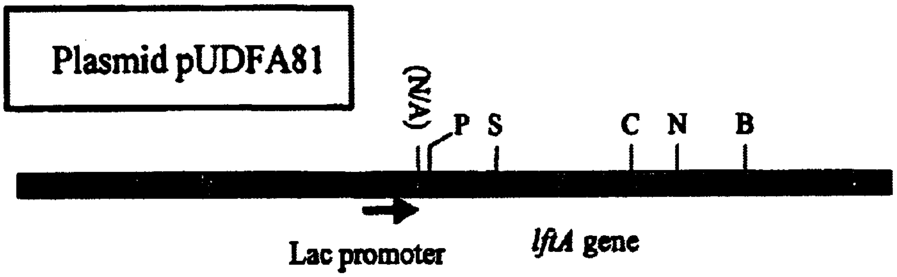
FIG. 7 shows a structure of the recombinant expression vector pUDFA18 carrying the levan fructotransferase gene, in which B stand for BamHI, P for PstI, N for NcoI, S for SalI, C for ClaI, and (N/A) for NcoI/AflII.
Figure 8:
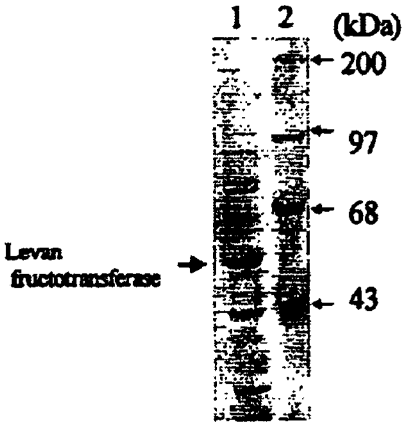
FIG. 8 shows the total protein pattern of *E. coli* JUD81 in SDS-PAGE in which a bacterial protein is electrophoresed in lane 1 and a standard protein in lane 2.

Development of Highly Expressable, Transformed *E. coli* Carrying Recombinant Levan Fructotransferase Gene Using the restriction enzyme PstI, the lftA gene was cut at its signal sequence, followed by Klenow treatment to give a blunt end. The lftA gene was divided by cutting with NotI. The Klenow-treated DNA fragment was further digested with SmaI and ligated to the pUC118 vector which was previously treated with CIP, so as to construct pUDFA18. This was introduced into *E. coli* DH5α. FIG. 7 shows the plasmid pUDFA18 which is obtained by inserting the lftA gene in the expression vector pUC118. FIG. 8 shows the total protein pattern of *E. Coli* JUD81 in SDS-PAGE. The *E. coli* JUD81 is the *E. coli* DH5 transformed with pUDFA18.

Experimental Example 8

Production of DFA IV from Levan by Use of Recombinant Levan Fructotransferase

Figure 9:
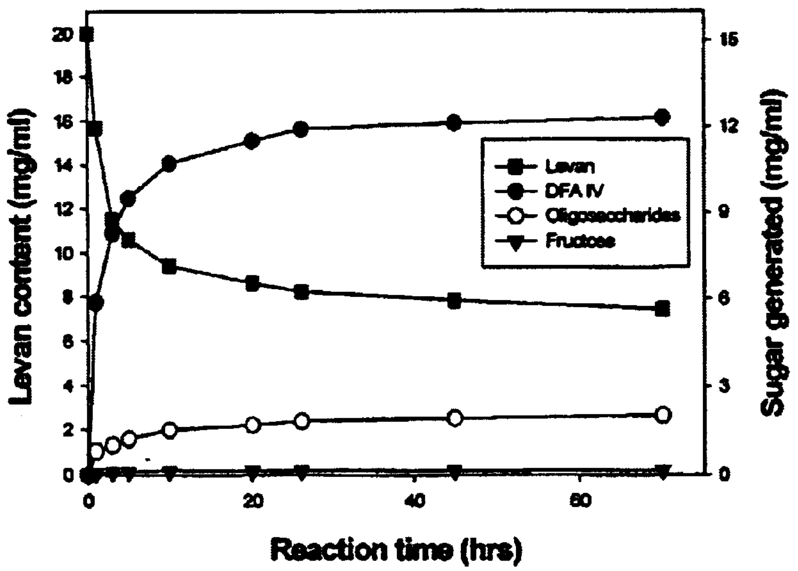
FIG. 9 shows the change of the amounts of DFA IV and other saccharides in the reaction mixture in accordance with the reaction time period.

In 1,000 ml of warm water was dissolved 20 g of levan, cooled and controlled to pH 6.5 with a phosphate buffer. To the resulting solution, *E. coli* JUD81 homogenate was added and allowed to react at 37° C. FIG. 9 shows the change of the amounts of DFA IV and other saccharides in the reaction mixture in accordance with reaction time period. After 40 hours of the reaction, the reaction mixture was allowed to stand in hot water for 5 min to inactivate the remaining enzyme and loaded onto a charcoal column (diameter 6.5 cm, height 20 cm). The column was washed with distilled water until no saccharides were detected in the washings. The column was again washed with 1,000 ml of 5% ethanol and then with 1,000 ml of 25% ethanol to elute the absorbed DFA IV. The effluents containing DFA IV were collected and concentrated to a volume of 30 ml by use of a rotary evaporator. To the concentrate, 100% ethanol was added to the final ethanol concentration of 95% or higher, so as to crystallize DFA IV. The DFA IV precipitates were washed many times with pure ethanol and dried to yield 2.5 g of pure DFA IV.

INDUSTRIAL APPLICABILITY

The analysis data from NMR, HPLC and TLC after acidolysis demonstrate that the DFA IV obtained is identical to a standard sample. FIG. 10 is a NMR result for the DFA IV obtained.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A polynucleotide of SEQ ID NO: 2 encoding for a levan fructotransferase of the amino acid SEQ ID NO: 1 isolated from *Arthrobacter ureafaciens* K2032, which can hydrolyze levan to produce difructose dianhydride IV.

2. A recombinant expression vector pUDFA81 carrying the polynucleotide sequence of SEQ ID NO: 2.

3. An organism *Escherichia coli* JUD81 KCTC 0877BP which is prepared by transforming *Escherichia coli* DH5α with the expression vector pUDFA81.

* * * * *

```
                          SEQUENCE LISTING


<160> NUMBER OF SEQ ID NOS: 4

<210> SEQ ID NO 1
<211> LENGTH: 521
<212> TYPE: PRT
<213> ORGANISM: Arthrobacter ureafaciens K2032

<400> SEQUENCE: 1

Met Thr Pro Ala Ile Ser Arg Arg Ala Val Leu Gln Gly Ala Gly Ala
1               5                   10                  15

Gly Ala Leu Ala Leu Ile Phe Gly Gly Ala Val Pro Pro Ala Ala Arg
            20                  25                  30

Ala Ser Ala Pro Gly Ser Leu Arg Ala Val Tyr His Met Thr Pro Pro
        35                  40                  45

Ser Gly Trp Leu Cys Asp Pro Gln Arg Pro Val Thr Thr His Gly Ala
    50                  55                  60

Tyr Gln Leu Tyr Tyr Leu His Ser Asp Gln Asn Asn Gly Pro Gly Gly
65                  70                  75                  80

Trp Asp His Ala Ser Thr Thr Asp Gly Val Ala Phe Thr His His Gly
                85                  90                  95

Thr Val Met Pro Leu Arg Pro Asp Phe Pro Val Trp Ser Gly Ser Ala
            100                 105                 110

Val Val Gly Thr Ala Asn Thr Ala Gly Phe Gly Ala Gly Ala Val Val
        115                 120                 125

Ala Leu Ala Thr Gln Pro Thr Asp Gly Val Arg Lys Tyr Gln Glu Gln
    130                 135                 140
```

-continued

```
Tyr Leu Tyr Trp Ser Thr Asp Gly Gly Phe Thr Phe Thr Ala Leu Pro
145                 150                 155                 160

Asp Pro Val Ile Val Asn Thr Asp Gly Arg Ala Ala Thr Thr Pro Ala
                165                 170                 175

Glu Ile Glu Asn Ala Glu Trp Phe Arg Asp Pro Lys Ile His Trp Asp
            180                 185                 190

Thr Ala Arg Gly Glu Trp Val Cys Val Ile Gly Arg Leu Arg Tyr Ala
        195                 200                 205

Ala Phe Tyr Thr Ser Pro Asn Leu Arg Asp Trp Thr Leu Arg Arg Asn
    210                 215                 220

Phe Asp Tyr Pro Asn His Ala Leu Gly Gly Ile Glu Cys Pro Asp Leu
225                 230                 235                 240

Phe Glu Ile Thr Ala Asp Asp Gly Thr Arg His Trp Val Leu Ala Ala
                245                 250                 255

Ser Met Asp Ala Tyr Gly Ile Gly Leu Pro Met Thr Tyr Ala Tyr Trp
            260                 265                 270

Thr Gly Thr Trp Asp Gly Glu Gln Phe His Ala Asp Asp Leu Thr Pro
        275                 280                 285

Gln Trp Leu Asp Trp Gly Trp Asp Trp Tyr Ala Ala Val Thr Trp Pro
    290                 295                 300

Ser Ile Asp Ala Pro Glu Thr Lys Arg Leu Ala Ile Ala Trp Met Asn
305                 310                 315                 320

Asn Trp Lys Tyr Ala Ala Arg Asp Val Pro Thr Asp Ala Ser Asp Gly
                325                 330                 335

Tyr Asn Gly Gln Asn Ser Ile Val Arg Glu Leu Arg Leu Ala Arg Gln
            340                 345                 350

Pro Gly Gly Trp Tyr Thr Leu Leu Ser Thr Pro Val Ala Ala Leu Thr
        355                 360                 365

Asn Tyr Val Thr Ala Thr Thr Thr Leu Pro Asp Arg Thr Val Asp Gly
    370                 375                 380

Ser Ala Val Leu Pro Trp Asn Gly Arg Ala Tyr Glu Ile Glu Leu Asp
385                 390                 395                 400

Ile Ala Trp Asp Thr Ala Thr Asn Val Gly Ile Ser Val Gly Arg Ser
                405                 410                 415

Pro Asp Gly Thr Arg His Thr Asn Ile Gly Lys Tyr Gly Ala Asp Leu
            420                 425                 430

Tyr Val Asp Arg Gly Pro Ser Asp Leu Ala Gly Tyr Ser Leu Ala Pro
        435                 440                 445

Tyr Ser Arg Ala Ala Ala Pro Ile Asp Pro Gly Ala Arg Ser Val His
    450                 455                 460

Leu Arg Ile Leu Val Asp Thr Gln Ser Val Glu Val Phe Val Asn Ala
465                 470                 475                 480

Gly His Thr Val Leu Ser Gln Gln Val His Phe Ala Glu Gly Asp Thr
                485                 490                 495

Gly Ile Ser Leu Tyr Thr Asp Gly Gly Pro Ala His Phe Thr Gly Ile
            500                 505                 510

Val Val Arg Glu Ile Gly Gln Ala Ile
        515                 520
```

<210> SEQ ID NO 2
<211> LENGTH: 2001
<212> TYPE: DNA
<213> ORGANISM: Arthrobacter ureafaciens K2032

-continued

<400> SEQUENCE: 2

```
gcggtgcacc ccgacttccc ctcgacgacc accgtccccc taccggccga ccgcccggcc     60
cgactgctcc tcagcctaga cgggcccctc ctcgaggtct tcgtcgggga cggtgaggcg    120
actgcgtcga acctggtcct cctgggggcc ggcggtgtga ccgcgagcct cgagacggca    180
cggccaggaa ccgtgcacgt gaccgcgatc gacgtcgagg cgcccagcga tgctgacgcc    240
cctgaacctg ccgccgttct gggctgacga gcgctcccac cccgacagct ctccttctac    300
cgctgcccga accagggtgg acgcttcgtc gcgcccaccc gtccacgaga ggaaccagca    360
atgacgccgg ccatctcacg ccgcgccgtg ctccagggag ccggcgccgg agcactcgcc    420
ctgatcttcg gcggtgctgt gccgcctgca gcccgggcat ccgctccggg ctcgctccgt    480
gccgtctacc acatgacgcc ccccagcggc tggctctgcg acccccaacg cccggtcacc    540
acccacggcg cctaccagct gtactacctg cactccgacc agaacaacgg ccccggcggc    600
tgggaccacg cgagcacgac cgacggcgtc gccttcacgc accacggcac cgtgatgccg    660
ctgcggcccg acttccccgt gtggtccggg tcggcggtcg tcggcaccgc gaacacggca    720
gggttcggcg ccggcgcggt cgtcgcgctc gcgacccagc cgaccgacgg cgtccgcaag    780
taccaggagc agtacctcta ctggtcgacc gacggcgggt tcacgttcac cgccctgccc    840
gaccccgtca tcgtcaacac cgacggtcgc gccgccacca cgcccgccga gatcgagaac    900
gccgagtggt tccgcgaccc caagatccac tgggacaccg cccgcggaga atgggtctgc    960
gtcatcggac gactgcggta cgccgcgttc tacacctcgc cgaacctgcg cgactggaca   1020
cttcgccgca acttcgacta cccgaaccac gccctcggcg gcatcgagtg ccccgacctg   1080
ttcgagatca ccgcagacga cgggacacgc cactgggtgc tcgccgccag catggacgcc   1140
tacggcatcg gcctccccat gacgtacgcc tactggacag gcacctggga cggcgagcag   1200
ttccacgccg acgacctcac ccgcaatgg ctcgactggg gctgggactg gtacgcggcc   1260
gtcacctggc catcgatcga cgcgcccgag accaagcgcc tcgccatcgc gtggatgaac   1320
aactggaagt acgccgcacg cgacgtcccc accgacgcat ccgacggcta caacgggcag   1380
aactcgatcg tccgcgagct gcggctcgcc cgacagcctg gcggctggta caccctcctg   1440
agcacccccg tggcagcgct gacgaactac gtcaccgcca ccaccacact ccccgaccgg   1500
accgtcgacg gcagcgccgt cctgccatgg aacggacgcg catacgagat cgagctcgac   1560
atcgcctggg acaccgcgac gaacgtcggc atctcggtgg gccgctcccc cgacggaacc   1620
cggcacacga acatcggcaa gtacggagca gacctgtacg tcgaccgagg accctccgac   1680
ctcgccgggt actcgctcgc cccctactcg cgagccgccg cccccatcga ccccggcgcc   1740
cgatccgtgc acctgcgcat cctcgtcgac acccagagcg tcgaggtctt cgtcaacgcc   1800
ggccacaccg tgctctccca gcaggtccac ttcgccgagg gcgacacggg aatctcgctc   1860
tacaccgacg gcggccccgc acacttcacc ggcatcgtcg tccgcgagat tggccaggcg   1920
atctaggcga tgcacaccac accgctcacc gaagccgcgc cccgggagac gacggccgac   1980
aatcgacacg tcctcgtcgt t                                             2001
```

<210> SEQ ID NO 3
<211> LENGTH: 2001
<212> TYPE: DNA
<213> ORGANISM: Arthrobacter ureafaciens K2032
<220> FEATURE:
<221> NAME/KEY: CDS
<222> LOCATION: (361)..(1917)
<223> OTHER INFORMATION:

-continued

<400> SEQUENCE: 3

```
gcggtgcacc ccgacttccc ctcgacgacc accgtccccc taccggccga ccgcccggcc     60

cgactgctcc tcagcctaga cgggcccctc ctcgaggtct tcgtcgggga cggtgaggcg    120

actgcgtcga acctggtcct cctgggggcc ggcggtgtga ccgcgagcct cgagacggca    180

cggccaggaa ccgtgcacgt gaccgcgatc gacgtcgagg cgcccagcga tgctgacgcc    240

cctgaacctg ccgccgttct gggctgacga gcgctcccac cccgacagct ctccttctac    300

cgctgcccga accagggtgg acgcttcgtc gcgcccaccc gtccacgaga ggaaccagca    360

atg acg ccg gcc atc tca cgc cgc gcc gtg ctc cag gga gcc ggc gcc      408
Met Thr Pro Ala Ile Ser Arg Arg Ala Val Leu Gln Gly Ala Gly Ala
1               5                   10                  15

gga gca ctc gcc ctg atc ttc ggc ggt gct gtg ccg cct gca gcc cgg      456
Gly Ala Leu Ala Leu Ile Phe Gly Gly Ala Val Pro Pro Ala Ala Arg
            20                  25                  30

gca tcc gct ccg ggc tcg ctc cgt gcc gtc tac cac atg acg ccc ccc      504
Ala Ser Ala Pro Gly Ser Leu Arg Ala Val Tyr His Met Thr Pro Pro
        35                  40                  45

agc ggc tgg ctc tgc gac ccc caa cgc ccg gtc acc acc cac ggc gcc      552
Ser Gly Trp Leu Cys Asp Pro Gln Arg Pro Val Thr Thr His Gly Ala
    50                  55                  60

tac cag ctg tac tac ctg cac tcc gac cag aac aac ggc ccc ggc ggc      600
Tyr Gln Leu Tyr Tyr Leu His Ser Asp Gln Asn Asn Gly Pro Gly Gly
65                  70                  75                  80

tgg gac cac gcg agc acg acc gac ggc gtc gcc ttc acg cac cac ggc      648
Trp Asp His Ala Ser Thr Thr Asp Gly Val Ala Phe Thr His His Gly
                85                  90                  95

acc gtg atg ccg ctg cgg ccc gac ttc ccc gtg tgg tcc ggg tcg gcg      696
Thr Val Met Pro Leu Arg Pro Asp Phe Pro Val Trp Ser Gly Ser Ala
            100                 105                 110

gtc gtc ggc acc gcg aac acg gca ggg ttc ggc gcc ggc gcg gtc gtc      744
Val Val Gly Thr Ala Asn Thr Ala Gly Phe Gly Ala Gly Ala Val Val
        115                 120                 125

gcg ctc gcg acc cag ccg acc gac ggc gtc cgc aag tac cag gag cag      792
Ala Leu Ala Thr Gln Pro Thr Asp Gly Val Arg Lys Tyr Gln Glu Gln
    130                 135                 140

tac ctc tac tgg tcg acc gac ggc ggg ttc acg ttc acc gcc ctg ccc      840
Tyr Leu Tyr Trp Ser Thr Asp Gly Gly Phe Thr Phe Thr Ala Leu Pro
145                 150                 155                 160

gac ccc gtc atc gtc aac acc gac ggt cgc gcc gcc acc acg ccc gcc      888
Asp Pro Val Ile Val Asn Thr Asp Gly Arg Ala Ala Thr Thr Pro Ala
                165                 170                 175

gag atc gag aac gcc gag tgg ttc cgc gac ccc aag atc cac tgg gac      936
Glu Ile Glu Asn Ala Glu Trp Phe Arg Asp Pro Lys Ile His Trp Asp
            180                 185                 190

acc gcc cgc gga gaa tgg gtc tgc gtc atc gga cga ctg cgg tac gcc      984
Thr Ala Arg Gly Glu Trp Val Cys Val Ile Gly Arg Leu Arg Tyr Ala
        195                 200                 205

gcg ttc tac acc tcg ccg aac ctg cgc gac tgg aca ctt cgc cgc aac     1032
Ala Phe Tyr Thr Ser Pro Asn Leu Arg Asp Trp Thr Leu Arg Arg Asn
    210                 215                 220

ttc gac tac ccg aac cac gcc ctc ggc ggc atc gag tgc ccc gac ctg     1080
Phe Asp Tyr Pro Asn His Ala Leu Gly Gly Ile Glu Cys Pro Asp Leu
225                 230                 235                 240

ttc gag atc acc gca gac gac ggg aca cgc cac tgg gtg ctc gcc gcc     1128
Phe Glu Ile Thr Ala Asp Asp Gly Thr Arg His Trp Val Leu Ala Ala
                245                 250                 255
```

-continued

```
agc atg gac gcc tac ggc atc ggc ctc ccc atg acg tac gcc tac tgg      1176
Ser Met Asp Ala Tyr Gly Ile Gly Leu Pro Met Thr Tyr Ala Tyr Trp
            260                 265                 270

aca ggc acc tgg gac ggc gag cag ttc cac gcc gac gac ctc acc ccg      1224
Thr Gly Thr Trp Asp Gly Glu Gln Phe His Ala Asp Asp Leu Thr Pro
        275                 280                 285

caa tgg ctc gac tgg ggc tgg gac tgg tac gcg gcc gtc acc tgg cca      1272
Gln Trp Leu Asp Trp Gly Trp Asp Trp Tyr Ala Ala Val Thr Trp Pro
    290                 295                 300

tcg atc gac gcg ccc gag acc aag cgc ctc gcc atc gcg tgg atg aac      1320
Ser Ile Asp Ala Pro Glu Thr Lys Arg Leu Ala Ile Ala Trp Met Asn
305                 310                 315                 320

aac tgg aag tac gcc gca cgc gac gtc ccc acc gac gca tcc gac ggc      1368
Asn Trp Lys Tyr Ala Ala Arg Asp Val Pro Thr Asp Ala Ser Asp Gly
                325                 330                 335

tac aac ggg cag aac tcg atc gtc cgc gag ctg cgg ctc gcc cga cag      1416
Tyr Asn Gly Gln Asn Ser Ile Val Arg Glu Leu Arg Leu Ala Arg Gln
            340                 345                 350

cct ggc ggc tgg tac acc ctc ctg agc acc ccc gtg gca gcg ctg acg      1464
Pro Gly Gly Trp Tyr Thr Leu Leu Ser Thr Pro Val Ala Ala Leu Thr
        355                 360                 365

aac tac gtc acc gcc acc acc aca ctc ccc gac cgg acc gtc gac ggc      1512
Asn Tyr Val Thr Ala Thr Thr Thr Leu Pro Asp Arg Thr Val Asp Gly
    370                 375                 380

agc gcc gtc ctg cca tgg aac gga cgc gca tac gag atc gag ctc gac      1560
Ser Ala Val Leu Pro Trp Asn Gly Arg Ala Tyr Glu Ile Glu Leu Asp
385                 390                 395                 400

atc gcc tgg gac acc gcg acg aac gtc ggc atc tcg gtg ggc cgc tcc      1608
Ile Ala Trp Asp Thr Ala Thr Asn Val Gly Ile Ser Val Gly Arg Ser
                405                 410                 415

ccc gac gga acc cgg cac acg aac atc ggc aag tac gga gca gac ctg      1656
Pro Asp Gly Thr Arg His Thr Asn Ile Gly Lys Tyr Gly Ala Asp Leu
            420                 425                 430

tac gtc gac cga gga ccc tcc gac ctc gcc ggg tac tcg ctc gcc ccc      1704
Tyr Val Asp Arg Gly Pro Ser Asp Leu Ala Gly Tyr Ser Leu Ala Pro
        435                 440                 445

tac tcg cga gcc gcc gcc ccc atc gac ccc ggc gcc cga tcc gtg cac      1752
Tyr Ser Arg Ala Ala Ala Pro Ile Asp Pro Gly Ala Arg Ser Val His
    450                 455                 460

ctg cgc atc ctc gtc gac acc cag agc gtc gag gtc ttc gtc aac gcc      1800
Leu Arg Ile Leu Val Asp Thr Gln Ser Val Glu Val Phe Val Asn Ala
465                 470                 475                 480

ggc cac acc gtg ctc tcc cag cag gtc cac ttc gcc gag ggc gac acg      1848
Gly His Thr Val Leu Ser Gln Gln Val His Phe Ala Glu Gly Asp Thr
                485                 490                 495

gga atc tcg ctc tac acc gac ggc ggc ccc gca cac ttc acc ggc atc      1896
Gly Ile Ser Leu Tyr Thr Asp Gly Gly Pro Ala His Phe Thr Gly Ile
            500                 505                 510

gtc gtc cgc gag att ggc cag gcgatctagg cgatgcacac cacaccgctc         1947
Val Val Arg Glu Ile Gly Gln
        515

accgaagccg cgccccggga gacgacggcc gacaatcgac acgtcctcgt cgtt          2001


<210> SEQ ID NO 4
<211> LENGTH: 519
<212> TYPE: PRT
<213> ORGANISM: Arthrobacter ureafaciens K2032

<400> SEQUENCE: 4

Met Thr Pro Ala Ile Ser Arg Arg Ala Val Leu Gln Gly Ala Gly Ala
```

-continued

```
1               5                   10                  15

Gly Ala Leu Ala Leu Ile Phe Gly Gly Ala Val Pro Pro Ala Ala Arg
            20                  25                  30

Ala Ser Ala Pro Gly Ser Leu Arg Ala Val Tyr His Met Thr Pro Pro
        35                  40                  45

Ser Gly Trp Leu Cys Asp Pro Gln Arg Pro Val Thr Thr His Gly Ala
    50                  55                  60

Tyr Gln Leu Tyr Tyr Leu His Ser Asp Gln Asn Asn Gly Pro Gly Gly
65                  70                  75                  80

Trp Asp His Ala Ser Thr Thr Asp Gly Val Ala Phe Thr His His Gly
                85                  90                  95

Thr Val Met Pro Leu Arg Pro Asp Phe Pro Val Trp Ser Gly Ser Ala
            100                 105                 110

Val Val Gly Thr Ala Asn Thr Ala Gly Phe Gly Ala Gly Ala Val Val
        115                 120                 125

Ala Leu Ala Thr Gln Pro Thr Asp Gly Val Arg Lys Tyr Gln Glu Gln
    130                 135                 140

Tyr Leu Tyr Trp Ser Thr Asp Gly Gly Phe Thr Phe Thr Ala Leu Pro
145                 150                 155                 160

Asp Pro Val Ile Val Asn Thr Asp Gly Arg Ala Ala Thr Thr Pro Ala
                165                 170                 175

Glu Ile Glu Asn Ala Glu Trp Phe Arg Asp Pro Lys Ile His Trp Asp
            180                 185                 190

Thr Ala Arg Gly Glu Trp Val Cys Val Ile Gly Arg Leu Arg Tyr Ala
        195                 200                 205

Ala Phe Tyr Thr Ser Pro Asn Leu Arg Asp Trp Thr Leu Arg Arg Asn
    210                 215                 220

Phe Asp Tyr Pro Asn His Ala Leu Gly Gly Ile Glu Cys Pro Asp Leu
225                 230                 235                 240

Phe Glu Ile Thr Ala Asp Asp Gly Thr Arg His Trp Val Leu Ala Ala
                245                 250                 255

Ser Met Asp Ala Tyr Gly Ile Gly Leu Pro Met Thr Tyr Ala Tyr Trp
            260                 265                 270

Thr Gly Thr Trp Asp Gly Glu Gln Phe His Ala Asp Asp Leu Thr Pro
        275                 280                 285

Gln Trp Leu Asp Trp Gly Trp Asp Trp Tyr Ala Ala Val Thr Trp Pro
    290                 295                 300

Ser Ile Asp Ala Pro Glu Thr Lys Arg Leu Ala Ile Ala Trp Met Asn
305                 310                 315                 320

Asn Trp Lys Tyr Ala Ala Arg Asp Val Pro Thr Asp Ala Ser Asp Gly
                325                 330                 335

Tyr Asn Gly Gln Asn Ser Ile Val Arg Glu Leu Arg Leu Ala Arg Gln
            340                 345                 350

Pro Gly Gly Trp Tyr Thr Leu Leu Ser Thr Pro Val Ala Ala Leu Thr
        355                 360                 365

Asn Tyr Val Thr Ala Thr Thr Thr Leu Pro Asp Arg Thr Val Asp Gly
    370                 375                 380

Ser Ala Val Leu Pro Trp Asn Gly Arg Ala Tyr Glu Ile Glu Leu Asp
385                 390                 395                 400

Ile Ala Trp Asp Thr Ala Thr Asn Val Gly Ile Ser Val Gly Arg Ser
                405                 410                 415

Pro Asp Gly Thr Arg His Thr Asn Ile Gly Lys Tyr Gly Ala Asp Leu
            420                 425                 430
```

-continued

```
Tyr Val Asp Arg Gly Pro Ser Asp Leu Ala Gly Tyr Ser Leu Ala Pro
        435                 440                 445

Tyr Ser Arg Ala Ala Ala Pro Ile Asp Pro Gly Ala Arg Ser Val His
    450                 455                 460

Leu Arg Ile Leu Val Asp Thr Gln Ser Val Glu Val Phe Val Asn Ala
465                 470                 475                 480

Gly His Thr Val Leu Ser Gln Gln Val His Phe Ala Glu Gly Asp Thr
                485                 490                 495

Gly Ile Ser Leu Tyr Thr Asp Gly Gly Pro Ala His Phe Thr Gly Ile
            500                 505                 510

Val Val Arg Glu Ile Gly Gln
        515
```